United States Patent
Nell et al.

(10) Patent No.: US 8,703,934 B2
(45) Date of Patent: Apr. 22, 2014

(54) SUBSTITUTED 4-AMINO-3,5-DICYANO-2-THIOPYRIDINES AND USE THEREOF

(75) Inventors: Peter Nell, Wuppertal (DE); Nicole Diedrichs, Velbert (DE); Barbara Albrecht-Küpper, Wülfrath (DE); Alexandros Vakalopoulos, Hilden (DE); Frank Süßmeier, Wuppertal (DE); Joerg Keldenich, Wuppertal (DE)

(73) Assignee: Bayer Intellectual Property GmbH, Monheim (DE)

( * ) Notice: Subject to any disclaimer, the term of this patent is extended or adjusted under 35 U.S.C. 154(b) by 498 days.

(21) Appl. No.: 12/516,939

(22) PCT Filed: Nov. 17, 2007

(86) PCT No.: PCT/EP2007/009963
§ 371 (c)(1),
(2), (4) Date: Nov. 24, 2009

(87) PCT Pub. No.: WO2008/064789
PCT Pub. Date: Jun. 5, 2008

(65) Prior Publication Data
US 2010/0069363 A1    Mar. 18, 2010

(30) Foreign Application Priority Data
Dec. 1, 2006  (DE) .......................... 10 2006 056 739

(51) Int. Cl.
*C07D 345/00*    (2006.01)
*C07D 517/00*    (2006.01)

(52) U.S. Cl.
USPC .......... 540/1; 540/597; 514/217.04; 514/316; 514/318; 514/342; 514/253; 514/236.8; 546/269.7; 546/256; 546/194; 546/193; 544/364; 544/124

(58) Field of Classification Search
USPC ................. 514/217.04, 316, 318, 342, 253.1, 514/236.8; 546/269.7, 256, 194, 1, 93; 544/364, 124
See application file for complete search history.

(56) References Cited

U.S. PATENT DOCUMENTS

| | | | |
|---|---|---|---|
| 4,052,510 A | 10/1977 | Simpson et al. | |
| 5,670,525 A | 9/1997 | Urbahns et al. | |
| 5,889,002 A | 3/1999 | Nielsen et al. | |
| 6,191,280 B1 | 2/2001 | Hamprecht et al. | |
| 6,693,102 B2 | 2/2004 | Stasch et al. | |
| 6,706,717 B2 | 3/2004 | Barrish et al. | |
| 6,743,798 B1 | 6/2004 | Straub et al. | |
| 6,833,364 B1 | 12/2004 | Straub et al. | |
| 6,864,287 B1 | 3/2005 | Alonso-Alija et al. | |
| 7,045,631 B2 | 5/2006 | Rosentreter et al. | |
| 7,078,417 B2 | 7/2006 | Rosentreter et al. | |
| 7,109,218 B2 | 9/2006 | Rosentreter et al. | |
| 7,129,255 B2 | 10/2006 | Rosentreter et al. | |
| 7,135,486 B1 | 11/2006 | Rosentreter et al. | |
| 7,173,036 B2 | 2/2007 | Sircar et al. | |
| 7,173,037 B2 | 2/2007 | Alonso-Alija et al. | |
| 7,186,716 B2 | 3/2007 | Wei et al. | |
| 7,674,825 B2 | 3/2010 | Alonso-Alija et al. | |
| 7,692,017 B2 | 4/2010 | Dinsmore et al. | |
| 7,705,043 B2 | 4/2010 | Alonso-Alija et al. | |
| 7,709,504 B2 | 5/2010 | Krahn et al. | |
| 7,781,470 B2 | 8/2010 | Alonso-Alija et al. | |
| 7,855,219 B2 | 12/2010 | Rosentreter et al. | |
| 7,932,259 B2 | 4/2011 | Nakazato et al. | |
| 7,951,811 B2 | 5/2011 | Nakazato et al. | |
| 2003/0232860 A1* | 12/2003 | Harada et al. ................. 514/332 |
| 2004/0162427 A1 | 8/2004 | Rosentreter et al. | |
| 2004/0176446 A1 | 9/2004 | Alonso-Alija et al. | |
| 2005/0182105 A1 | 8/2005 | Nirschl et al. | |
| 2005/0227972 A1 | 10/2005 | Rosentreter et al. | |
| 2006/0154969 A1 | 7/2006 | Rosentreter et al. | |
| 2007/0066630 A1 | 3/2007 | Palani et al. | |
| 2007/0213372 A1 | 9/2007 | Rosentreter et al. | |
| 2007/0293670 A1 | 12/2007 | Nakazato et al. | |
| 2008/0269300 A1 | 10/2008 | Erguden et al. | |
| 2009/0221649 A1 | 9/2009 | Krahn et al. | |
| 2010/0009973 A1 | 1/2010 | Rhodes et al. | |
| 2010/0022544 A1 | 1/2010 | Nell et al. | |
| 2010/0048641 A1 | 2/2010 | Nell et al. | |

(Continued)

FOREIGN PATENT DOCUMENTS

| | | | |
|---|---|---|---|
| EP | 0608565 A1 | 12/1993 | |
| EP | 1302463 A1 | 4/2003 | |

(Continued)

OTHER PUBLICATIONS

Vippagunta et al., Advanced Drug Defivery Reviews, vol. 48, p. 3-26 (on p. 3), 2001.*
Sheridan, J. Chem. Inf. Sci. 2002, 42, 103-108 as applied to claims 1-3, 6, 9, 11 and 12.*
Martyn et al. ("Obesity-induced Insulin Resistance and Hyperglycemia: Etiologic Factors and Molecular Mechanisms"; 2008; Anesthesiology; Warner, et al., Eds.; 109:137-48).*
Patani et al, Chem. Rev. 1996, 96, 3147-3176.*
M. E. Olah et al.: "Cloning, Expression, and Characterization of the Unique Bovine $A_1$ Adenosine Receptor," The Journal of Biological Chemistry, vol. 367, No. 15, May 25, 1991, pp. 10764-10770.

(Continued)

*Primary Examiner* — Brandon Fetterolf
*Assistant Examiner* — Jean Cornet
(74) *Attorney, Agent, or Firm* — Karen B. King; Thomas C. Blankinship

(57) ABSTRACT

The present application relates to novel substituted 4-amino-3,5-dicyano-2-thiopyridine derivatives, to processes for their preparation, to their use for the treatment and/or prophylaxis of diseases and to their use for preparing medicaments for the treatment and/or prophylaxis of diseases, preferably for the treatment and/or prevention of hypertension and other cardiovascular disorders.

6 Claims, No Drawings

(56) References Cited

U.S. PATENT DOCUMENTS

| | | |
|---|---|---|
| 2010/0093728 A1 | 4/2010 | Nell et al. |
| 2010/0197609 A1 | 8/2010 | Vakalopoulos et al. |
| 2011/0130377 A1 | 6/2011 | Nell et al. |
| 2011/0136871 A1 | 6/2011 | Hubsch et al. |
| 2011/0207698 A1 | 8/2011 | Meibom et al. |
| 2011/0294718 A1 | 12/2011 | Lerchen et al. |
| 2011/0294719 A1 | 12/2011 | Lerchen et al. |

FOREIGN PATENT DOCUMENTS

| | | |
|---|---|---|
| JP | 09-132529 | 5/1997 |
| JP | 10-324687 | 12/1998 |
| JP | 2003-183254 | 7/2003 |
| WO | 95/34563 | 12/1995 |
| WO | 97/27177 A2 | 7/1997 |
| WO | 99/03861 A1 | 1/1999 |
| WO | WO-99/32117 A1 | 7/1999 |
| WO | WO-01/25210 A2 | 4/2001 |
| WO | WO 01/62233 | 8/2001 |
| WO | WO-01/62233 A2 | 8/2001 |
| WO | 02/48115 A2 | 6/2002 |
| WO | WO-02/50071 A1 | 6/2002 |
| WO | WO 02/070485 | 9/2002 |
| WO | WO-02/070485 A1 | 9/2002 |
| WO | WO-03/053441 A1 | 7/2003 |
| WO | 03/091246 | 11/2003 |
| WO | 2004/014372 A1 | 2/2004 |
| WO | WO-2004/054505 A2 | 7/2004 |
| WO | 2005/007647 A1 | 1/2005 |
| WO | WO-2005/046603 A2 | 5/2005 |
| WO | WO-2006/027142 A1 | 3/2006 |
| WO | WO-2006/034446 A2 | 3/2006 |
| WO | 2007/073855 | 2/2009 |

OTHER PUBLICATIONS

K-N. Klotz et al.: "Comparartive Pharmacology of Human Adenosine Receptor Subtypes—Characterization of Stably Transfected Receptors in CHO Cells," Naunyn-Schmiedeberg's Arch Pharmacol, 357, 1998, pp. 1-9.

S-A Poulsen et al.: "Adenosine Receptors: New Opportunities for Future Drugs," Bioorganic & Medicinal Chemistry, 6, 1998, pp. 619-641.

Beukers, M.W. et al., "New, Non-Adenosine, High-Potency Agonists for the Human Adenosine $A_{2B}$ Receptor with an Improved Selectivity Profile Compared to the Reference Agonist N-Ethylcarboxamidoadenosine", Journal of Medicinal Chemistry, Jul. 15, 2004; vol. 47, No. 15, pp. 3707-3709.

U.S. Appl. No. 13/2010,889, filed Aug. 16, 2011.

Anand, et al.:"Novel Dipeptide Prodrugs of Acyclovir for Ocular Herpes Infections: Bioreversion, Antiviral Activity and Transport Across Rabbit Cornea," Current Eye Research, Mar. 2003, 26 (3-4):151-163.

Avila, et al.: A1-, A2A- and A3-subtype adenosine receptors modulate intraocular pressure in the mouse, British Journal of Pharmacology, 2001, 134:241-245.

Barton et al.,:"Homologation of Acids via Carbon Radicals Generated from the Acyl Derivatives of N-Hydroxy-2-Thiopyrodine. (The Two-Carbon Problem)," Tetrahedron Letters, 1991, 32(28): 3309-3312.

Bauman:"Updating the Evidence that Physical Activity is Good for Health: An Epidemiological Review 2000-2003," J. Sci. Med. Sport, Apr. 2004, 7(1): Suppl:6-19.

Beaumont, et al.:"Design of Ester Prodrugs to Enhance Oral Absorption of Poorly Permeable Compounds: Challenges to the Discovery Scientist," Current Drug Metabolism, 2003, 4(6):461-485.

Beukers, et al.:"New, Non-Adenosine, High-Potency Agonists for the Human Adenosine A2B Receptor with an Improved Selectivity Profile Compared to the Reference Agonist N-Ethylcarboxamidoadenosine," Journal of Medicinal Chemistry, Jul. 15, 2004, 47(15): 3707-3709.

Bundgaard:"Design of Prodrugs: Bioreversible derivatives for various functional groups and chemical entities," Elsevier Science Publishers B.V., 1985, pp. 1-92.

Castedo, et al.:"Synthesis and Pharmacological Activity of Some Nitrofuraldehyde Cyanopyridine Derivatives," Eur. J. Med. Chem., 1984, 19(6):555-557, abstract retrieved from CAPLUS Accession No. 1985:437337, EPO Document XP002202946.

Cesar, et al.:"Trimethylsilyldiazomethane in the Preparation of Diazoketonesvia Mixed Anhydride and Coupling Reagent Methods: A New Approach to the Arndt-Eistert Synthesis," Tetrahedron Letters, 2001, 42: 7099-7102.

Crosson: "Intraocular Pressure Responses to the AdenosineAgonist Cyclohexyladenosine: Evidence for a DualMechanism of Action," IOVS, Jul. 2001, 42(8): 1837-1840.

Dhalla, et al.:"Pharmacology and Theraputic Applications of A1 Adenosine Receptor Ligands," Current Topics in Medicinal Chemisty, 2003, 3:369-385.

Dyachenko, et al.:"Single Stage Synthesis of 2-Alkylthio(seleno)-4-Hetaryl-3-cyano-5,6,7,8-Tetrahydroquinolines," Chemistry of Heterocyclic Compounds, 1997, 33(10): 1203-1208.

Dyachenko, et al.:"New Route to 6-Amino-4-aryl-3,5-dicyanopyridine-2(1H)-thiones," Russian Journal of Organic Chemistry,1997, 33(7):1014-1017.

Dyachenko, et al.:"Michael Reaction in SyntheSis of 6-Amino-4-(4-Butoxyphenyl)-3,5-Dicyanopyridine-2(1H)-thionene," Chemistry of Heterocyclic Compounds, 1998, 34(2):188-194.

Dyachenko:"Cyclohexanecarbaldehyde in Multicomponent Syntheses of Functionalized Cyclohexyl-Substituted Acrylonitriles, 4H-Chalcogenopyrans, 1,4-Dihydropyridines, and Pyridines," Russian Journal of General Chemistry, 2006, 76(2):282-291.

Dyachenko, et al.,:"Synthesis and Recyclization of 4-Aryl-2,6-diamino-3,5-dicyano-4H-thiopyrans," Russian Journal of Organic Chemistry, 1998, 34(4): 557-563.

Eissa, et al.:"Synthesis and Biological Evaluation of Pyrido[2,3-d]pyrimidine as Antitumor Effect," Egypt. J. Chem., 2006, 49(6):761-774.

Elnagdi, et al.:"Studies with Polyfunctionally Substituted Heterocycles: Synthesis of New Pyridines, Naphtho[1,2-b] pyrans, Pyrazolo[3,4]pyridines and Pyrazolo[1,5-a]pyrimidines," Z. Naturforsch, 1992, 47b:572-578.

El-Torgoman, et al.:"Nitriles in Heterocyclic Synthesis: The reaction of 2-Thiocarbamoyl Cinnamonitriles with Active Methylene Reagents," Z. Naturforsch., 1987, 42b:107-111.

Ettmayer, et al.:"Lessons Learned from Marketed and Investigational Prodrugs," J. Med. Chem., May 6, 2004, 47(10) 2393-2404.

Fuentes, et al.:"Heterocycle Synthesis. XVI. Reaction of Malononitrile with Benzylidenemalononitriles in Presence of Amines." An. Quim., Ser. C., 1980, 76(1): 68-69, English language abstract retrieved from CAPLUS Accession No. 1981:139574, EPO Document No. XP002202947.

Goto, et al.:"Studies on Azole Compounds.III.1 Reactions of Oxazole N-Oxides with Phosphoryl Chloride and Acetic Anhydride 2", Chem. Pharm. Bull. 1971, 19: 2050-2057.

Guillory:"Generation of Polymorphs, Hydrates, Solvates, and Amorphouse Solids," in Polymorphism in Pharmaceutical Solids (Ed. Brittain),1999, pp. 183-226, Marcel Dekker, Inc.

Ibrahim, et al.:"Synthesis and Biological Activity of Some New Heterocyclic Quinoline Derivatives," Phosphorus, Sulfer, and Silicon, 1991, 57: 293-301.

Jacobson, et al,:"Adenosine Receptors as Theraputic Targets," Nat. Rev. Drug Discover.,2005, 5:247-264.

Kambe, et al.:"Synthetic Studies Using $\alpha,\beta$-Unsaturated Nitriles: Facile Synthesis of Pyridine Derivatives," Synthesis Communications, Jul. 1981, pp: 531-533.

Klotz:"Adenosine Receptors and their Ligands," Naunyn-Schmiedeberg's Arch. Pharmacol., 2000, 362: 382-391.

Müller, et al.:"Adenosine Receptor Antagonists: Structures and Potential Therapeutic Applications," Current Pharmaceutical Design, 1996, 2:501-530.

Müller:"Adenosine Receptor Ligands-Recent Developments Part I. Agonists," Current Medicinal Chemistry, 2000, 7:1269-1288.

Müller:"Review. Cardiovascular & Renal. A1-Adenosine Receptor Antagonists," Exp. Opin. Ther. Patents, 1997, 7(5):419-440.

(56) References Cited

OTHER PUBLICATIONS

Inotek Pharmaceuticals Press Release, "Inotek Pharmaceuticals Initiates Multiple-Dose Phase 2 Clinical Trial of INO-8875 in Patients with Glaucoma," Jun. 17, 2010.

Patani, et al.: "Bioisosterism: A Rational Approach in Drug Design," Chem. Rev., 1996, 96:3147-3176.

Pflueger, et al.:"Role of Adenosine in Contrast Media-Induced Acute Renal Failure in Diabetes Mellitus," Mayo Clin Proc., Dec. 2000, 75(12):1275-1283.

Quintela, et al.:"Reactivity of Heterocyclic Compounds. V. Behavior of 6-alkoxy-2-amino-(or chloro)-4-aryl-3,5-dicyanopyridines in the Presence of Nucleophiles," Anales de Quimica, Serie C: Quimica Organica y Bioquimica, 1984, 80(3):268-72, English language abstract retrieved from CAPLUS Accession No. 1985:437345, CAPLUS Document No. 103:37345, EPO Document No. XP002202945.

Quintela, et al.:"Synthesis, Antihistaminic and Cytotoxic Activity of Pyridothieno- and Pyridodithienotriazines", Eur. J. Med. Chem, 1998, 33:887-897.

Rodinovskaya, et al.:"Substituted 4-(3-Cyanopyridin-2-ylthio)acetoacetates: New Convenient Reagents for the Synthesis of Heterocycles," Synthesis, 2006, (14): 2357-2370.

Rosenman:"Do Environmental Effects on Human Emotions Cause Cardiovascular Disorders?," Acta Physiologica Scandinavica, Supplement,1997, 161/640 (133-136), abstract retrieved from EMBASE Accession No. 97358868.

Ruhe, et al.:"Use of Antioxidant Nutrients in the Prevention and Treatment of Type 2 Diabetes," Journal of the American College of Nutrition, 2001, 20(5): 363S-369S.

Shams, et al.:"Nitriles in Organic Synthesis. New Routes for Synthesis of Pyridines and Azinothiopyrans," Journal fuer Praktische Chemie (Leipzig), 1988, 330(5):817-13, abstract retrieved from CAPLUS Accession No. 1989:497050.

Sheridan:"The Most Common Chemical Replacements in Drug-Like Compounds," J Chem. Inf. Comput. Sci., 2002, 42:103-108.

Suttner, et al.:"The Heart in the Elderly Critically Ill Patient," Curr. Opin. Crit. Care, Oct. 2002, 8(5):389-94, abstract retrieved from MEDLINE Accession No. 2002495386, PubMed ID: 12357105.

Szydlowski, et al.:"Biological Role of Chromium," Diabetologia Polska, 2003, 10(3):365-370, English language abstract retrieved from EMBASE Accession No. 2004016455.

Vasudevan A. et al., "Aminopiperidine indazoles as orally efficacious melanin concentrating hormone receptoer-1 antagonists," Bioorg. Med. Chem. Lett. 2005, 15 (23), 5293-5297.

Vippagunta, et al.:"Crystalline Solids," Advanced Drug Delivery Reviews, May 16, 2001, 48(1):3-26.

West:"Solid State Chemistry and its Applications," Wiley, New York, 1988, pp. 358 & 365.

Ye, et al.:Organic Synthesis with α-Diazocarbonyl Compounds, Chem. Rev. 1994, 94:1091-1160.

Yu, et al:"Physical Characterization of Polymorphic Drugs: An Integrated Characterization Strategy," Pharmaceutical Science & Technology Today, Jun. 1998, 1(3):118-127.

Zhu, G. et al., "Design and synthesis of pyridine-pyrazolopyridine-based inhibitors of protein kinase B/Akt," Bioorg. Med. Chem. 2007, 15 (6), 2441-2452.

* cited by examiner

SUBSTITUTED 4-AMINO-3,5-DICYANO-2-THIOPYRIDINES AND USE THEREOF

RELATED APPLICATIONS/PATENTS AND INCORPORATION BY REFERENCE

This application is a National Stage Application filed under 35 U.S.C. §371 based on International Application No. PCT/EP2007/009963, filed Nov. 17, 2007, which claims priority to German Patent Application Number 102006056739.0, filed Dec. 1, 2006, the entire contents each of which are incorporated herein by reference.

The foregoing applications, and all documents cited therein and all documents cited or referenced therein, and all documents cited or referenced herein, including any U.S. or foreign patents or published patent applications, International patent applications, as well as, any non-patent literature references and any manufacturer's instructions, are hereby expressly incorporated herein by reference.

The present application relates to novel substituted 4-amino-3,5-dicyano-2-thiopyridine derivatives, to processes for their preparation, to their use for the treatment and/or prophylaxis of diseases and to their use for preparing medicaments for the treatment and/or prophylaxis of diseases, preferably for the treatment and/or prevention of hypertension and other cardiovascular disorders.

Adenosine, a purine nucleoside, is present in all cells and is released by a large number of physiological and pathophysiological stimuli. Adenosine is formed intracellularly as an intermediate during the degradation of adenosine 5'-monophosphate (AMP) and S-adenosylhomocysteine, but it can be released from the cell, in which case it acts as a hormone-like substance or neurotransmitter by binding to specific receptors.

Under normoxic conditions, the concentration of free adenosine in the extracellular space is very low. However, under ischemic or hypoxic conditions, the extracellular concentration of adenosine in the affected organs is increased dramatically. Thus, it is known, for example, that adenosine inhibits platelet aggregation and increases the blood supply to the coronary arteries. Furthermore, it acts on the blood pressure, on the heart rate, on the release of neurotransmitters and on lymphocyte differentiation. In adipocytes, adenosine is capable of inhibiting lipolysis, thus lowering the concentration of free fatty acids and triglycerides in the blood.

The aim of these actions of adenosine is to increase the oxygen supply of the affected organs and/or to reduce the metabolism of these organs in order to adjust the metabolism of the organ to the blood supply of the organ under ischemic or hypoxic conditions.

The action of adenosine is mediated via specific receptors. To date, subtypes A1, A2a, A2b and A3 are known. According to the invention, "adenosine-receptor-selective ligands" are substances which bind selectively to one or more subtypes of the adenosine receptors, thus either mimicking the action of adenosine (adenosine agonists) or blocking its action (adenosine antagonists).

The actions of these adenosine receptors are mediated intracellularly by the messenger cAMP. In the case of the binding of adenosine to the A2a or A2b receptors, the intracellular cAMP is increased via activation of the membrane-bound adenylate cyclase, whereas binding of adenosine to the A1 or A3 receptors results in a decrease of the intracellular cAMP concentration via inhibition of adenylate cyclase.

In the cardiovascular system, the main consequences of the activation of adenosine receptors are: bradycardia, negative inotropism and protection of the heart against ischemia ("preconditioning") via A1 receptors, dilation of the blood vessels via A2a and A2b receptors and inhibition of the fibroblasts and smooth-muscle-cell proliferation via A2b receptors.

In the case of A1 agonists (coupling preferably via $G_i$ proteins), a decrease of the intracellular cAMP concentration is observed (preferably after direct prestimulation of adenylate cyclase by forskolin). Correspondingly, A2a and A2b agonists (coupling preferably via $G_s$ proteins) leads to an increase and A2a and A2b antagonists to a decrease of the cAMP concentration in the cells. In the case of A2 receptors, a direct prestimulation of adenylate cyclase by forskolin is of no benefit.

The activation of A2b receptors by adenosine or specific A2b agonists leads, via dilation of blood vessels, to lowering of the blood pressure. The lowering of the blood pressure is accompanied by a reflectory increase in heart rate. The increased heart rate can be reduced by activation of A1 receptors using specific A1 agonists.

The combined action of selective A1/A2b agonists on the vascular system and heart rate thus results in a systemic lowering of the blood pressure without relevant heart-rate increase. Dual A1/A2b agonists having such a pharmacological profile could be employed, for example, for treating hypertension in humans.

In adipocytes, the activation of A1 and A2b receptors leads to an inhibition of lipolysis. Thus, the combined action of A1/A2b agonists on lipid metabolism results in a lowering of free fatty acids and triglycerides. In turn, in patients suffering from metabolic syndrome and in diabetics, reducing lipids leads to lower insulin resistance and improved symptoms.

The abovementioned receptor selectivity can be determined by the effect of the substances on cell lines which, after stable transfection with the corresponding cDNA, express the receptor subtypes in question [see the publication M. E. Olah, H. Ren, J. Ostrowski, K. A. Jacobson, G. L. Stiles, "Cloning, expression, and characterization of the unique bovine A1 adenosine receptor. Studies on the ligand binding site by site-directed mutagenesis", *J. Biol. Chem.* 267 (1992), pages 10764-10770, the disclosure of which is hereby fully incorporated by way of reference].

The effect of the substances on such cell lines can be monitored by biochemical measurement of the intracellular messenger cAMP [see the publication K. N. Klotz, J. Hessling, J. Hegler, C. Owman, B. Kull, B. B. Fredholm, M. J. Lohse, "Comparative pharmacology of human adenosine receptor subtypes—characterization of stably transfected receptors in CHO cells", *Naunyn Schmiedebergs Arch. Pharmacol.* 357 (1998), pages 1-9, the disclosure of which is hereby fully incorporated by way of reference].

The "adenosine-receptor-specific" ligands known from the prior art are mainly derivatives based on natural adenosine [S.-A. Poulsen and R. J. Quinn, "Adenosine receptors: New opportunities for future drugs", *Bioorganic and Medicinal Chemistry* 6 (1998), pages 619-641]. However, most of these adenosine ligands known from the prior art have the disadvantage that their action is not really receptor-specific, that their activity is less than that of natural adenosine or that they have only very weak activity after oral administration. Thus, they are mainly used only for experimental purposes. Compounds of this type which are still in clinical development are hitherto only suitable for intravenous application.

WO 01/25210 and WO 02/070485 describe substituted 2-thio-3,5-dicyano-4-aryl-6-aminopyridines as adenosine receptor ligands for the treatment of disorders. WO 03/053441 discloses specifically substituted 2-thio-3,5-dicyano-4-phenyl-6-aminopyridines as selective ligands for the adenosine A1 receptor, and WO 2006/027142 claims substituted phenylaminothiazole derivatives as dual adenosine A1/A2b agonists for the treatment of hypertension and other cardiovascular disorders. However, it was found that some of these compounds have disadvantages with respect to their physicochemical and/or pharmacokinetic properties, such as, for example, their solubility in water and other physiological media or their resorption behavior in the body.

WO 01/62233 discloses various pyridine and pyrimidine derivatives and their use as adenosine receptor modulators. The use of substituted 3,5-dicyanopyridines as calcium-dependent potassium channel openers for treating urological disorders is described in EP 1 302 463-A1. Various heterocyclically substituted pyridine derivatives and their use for treating diseases are described in WO 99/32117, WO 2004/054505, WO 2005/046603 and WO 2006/034446. WO 02/50071 discloses aminothiazole derivatives as tyrosine kinase inhibitors for the treatment of cancer and also immuno-logical and allergic disorders.

It was an object of the present invention to provide novel compounds which act as selective agonists of the adenosine A1 receptor or as selective dual agonists of the adenosine A1 and A2b receptor and which, as such, are suitable for the treatment and/or prevention in particular of hypertension and other cardiovascular disorders, of metabolic syndrome, of diabetes and dyslipidemias and also for the protection of organs during transplantations and surgical interventions, and which additionally have an improved physicochemical and/or pharmacokinetic profile compared to the substances known from the prior art.

The present invention provides compounds of the formula (I)

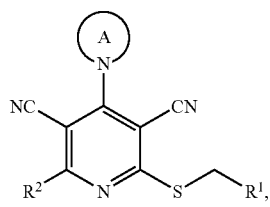

in which
ring A represents a 4- to 7-membered heterocycle which is attached via nitrogen and which may contain a further ring heteroatom from the group consisting of N, O and S and which may be
(i) substituted up to five times by identical or different substituents from the group consisting of $(C_1-C_4)$-alkyl which for its part may be mono- or disubstituted by identical or different substituents from the group consisting of oxo, hydroxyl, $(C_1-C_4)$-alkoxy, amino, mono-$(C_1-C_4)$-alkylamino, di-$(C_1-C_4)$-alkylamino and $(C_3-C_6)$-cycloalkyl,
and/or
(ii) mono- or disubstituted by identical or different substituents from the group consisting of oxo, thioxo, hydroxyl, $(C_1-C_4)$-alkoxy, amino, mono-$(C_1-C_4)$-alkylamino, di-$(C_1-C_4)$-alkylamino and $(C_3-C_6)$-cycloalkyl,
$R^1$ represents $(C_6-C_{10})$-aryl or 5- to 10-membered heteroaryl having up to three ring heteroatoms from the group consisting of N, O and S, each of which radicals may be
(i) mono- or disubstituted by identical or different radicals selected from the group consisting of halogen, nitro, cyano, $(C_1-C_6)$-alkyl, trifluoromethyl, hydroxyl, $(C_1$-$C_6)$-alkoxy, amino, mono-$(C_1-C_6)$-alkylamino, di-$(C_1$-$C_6)$-alkylamino, mono-$(C_2-C_6)$-alkenylamino, carboxyl, $(C_1-C_6)$-alkoxycarbonyl, carbamoyl, mono-$(C_1-C_6)$-alkylaminocarbonyl and di-$(C_1-C_6)$-alkylaminocarbonyl
and/or
(ii) substituted by pyrrolidino, piperidino, morpholino, piperazino, N'-$(C_1-C_4)$-alkylpiperazino or a group of the formula -L-$R^3$ in which
L represents a bond, NH or O
and
$R^3$ represents phenyl or 5- or 6-membered heteroaryl having up to three ring heteroatoms from the group consisting of N, O and S, each of which radicals may be mono- to trisubstituted by identical or different radicals selected from the group consisting of halogen, nitro, cyano, $(C_1-C_6)$-alkyl, trifluoromethyl, hydroxyl, $(C_1-C_6)$-alkoxy, difluoromethoxy, trifluoromethoxy, amino, mono-$(C_1-C_6)$-alkylamino, di-$(C_1-C_6)$-alkylamino, $(C_1-C_6)$-alkoxycarbonyl and carboxyl,
and
$R^2$ represents hydrogen or represents $(C_1-C_6)$-alkyl or $(C_1$-$C_6)$-alkoxy, each of which radicals may be substituted by hydroxyl, $(C_1-C_4)$-alkoxy, carboxyl, $(C_1-C_4)$-alkoxycarbonyl or up to three times by fluorine
or
$R^2$ represents a group of the formula —$NR^4R^5$ in which
$R^4$ and $R^5$ are identical or different and independently of one another represent hydrogen or $(C_1-C_6)$-alkyl which may be mono- or disubstituted by identical or different radicals from the group consisting of hydroxyl, $(C_1-C_4)$-alkoxy, amino, mono-$(C_1-C_4)$-alkylamino, di-$(C_1-C_4)$-alkylamino, carboxyl, $(C_1-C_4)$-alkoxycarbonyl and a 4- to 7-membered heterocycle,
where the heterocycle mentioned contains one or two ring heteroatoms from the group consisting of N, O and S and for its part may be mono- or disubstituted by identical or different radicals from the group consisting of $(C_1-C_4)$-alkyl, hydroxyl, oxo and $(C_1-C_4)$-alkoxy,
or
$R^5$ and $R^6$ together with the nitrogen atom, to which they are attached, form a 4- to 7-membered heterocycle which may contain a further ring heteroatom from the group consisting of N, O or S and may be mono- or disubstituted by identical or different radicals from the group consisting of $(C_1-C_4)$-alkyl, hydroxyl, oxo, $(C_1$-$C_4)$-alkoxy, azetidino, pyrrolidino, piperidino and morpholino, and N-oxides, salts, solvates, salts of the N-oxides and solvates of the N-oxides and salts thereof.

Compounds according to the invention are the compounds of the formula (I) and the salts, solvates and solvates of the salts thereof, the compounds which are encompassed by the formulae (I) and are mentioned in the formulae below, and the salts, solvates and solvates of the salts thereof, and the compounds which are encompassed by formula (I) and are mentioned below as exemplary embodiments, and the salts, solvates and solvates of the salts thereof, where the compounds which are encompassed by the formula (I) and are mentioned below are not already salts, solvates and solvates of the salts.

The compounds according to the invention may, depending on their structure, exist in stereoisomeric forms (enantiomers, diastereomers). The invention therefore encompasses the enantiomers or diastereomers and respective mixtures thereof. The stereoisomerically pure constituents can be isolated from such mixtures of enantiomers and/or diastereomers in a known manner.

Where the compounds according to the invention can exist in tautomeric forms, the present invention encompasses all tautomeric forms.

Salts preferred for the purposes of the present invention are physiologically acceptable salts of the compounds according to the invention. Also included are salts which are not themselves suitable for pharmaceutical applications but can be used, for example, for the isolation or purification of the compounds according to the invention.

Physiologically acceptable salts of the compounds according to the invention include acid addition salts of mineral acids, carboxylic acids and sulfonic acids, for example salts of hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, acetic acid, trifluoroacetic acid, propionic acid, lactic acid, tartaric acid, malic acid, citric acid, fumaric acid, maleic acid and benzoic acid.

Physiologically acceptable salts of the compounds according to the invention also include salts of conventional bases such as, by way of example and preferably, alkali metal salts (for example sodium and potassium salts), alkaline earth metal salts (for example calcium and magnesium salts) and ammonium salts derived from ammonia or organic amines having 1 to 16 carbon atoms, such as, by way of example and preferably, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

Solvates refer for the purposes of the invention to those forms of the compounds according to the invention which form a complex in the solid or liquid state through coordination with solvent molecules. Hydrates are a specific form of solvates in which the coordination takes place with water. For the purposes of the present invention, preferred solvates are hydrates.

In addition, the present invention also encompasses prodrugs of the compounds according to the invention. The term "prodrugs" encompasses compounds which for their part may be biologically active or inactive but are converted (for example metabolically or hydrolytically) into compounds according to the invention during their residence time in the body.

For the purposes of the present invention, the substituents have the following meaning, unless specified otherwise:

For the purposes of the invention, $(C_1-C_6)$-alkyl, $(C_1-C_4)$-alkyl and $(C_1-C_3)$-alkyl represent a straight-chain or branched alkyl radical having 1 to 6, 1 to 4 and 1 to 3 carbon atoms, respectively. Preference is given to a straight-chain or branched alkyl radical having 1 to 4, particularly preferably 1 to 3, carbon atoms. The following radicals may be mentioned by way of example and by way of preference: methyl, ethyl, n-propyl, isopropyl, n-butyl, isobutyl, sec-butyl, tert-butyl, 1-ethylpropyl, n-pentyl and n-hexyl.

For the purposes of the invention, $(C_2-C_6)$-alkenyl represents a straight-chain or branched alkenyl radical having 2 to 6 carbon atoms and one or two double bonds. Preference is given to a straight-chain or branched alkenyl radical having 2 to 4 carbon atoms and one double bond. The following radicals may be mentioned by way of example and by way of preference: vinyl, allyl, isopropenyl, 2-methylprop-2-en-1-yl, n-but-2-en-1-yl and n-but-3-en-1-yl.

For the purposes of the invention, $(C_3-C_6)$-cycloalkyl and $(C_3-C_5)$-cycloalkyl represent a monocyclic saturated carbocycle having 3 to 6 and 3 to 5 ring carbon atoms, respectively. The following radicals may be mentioned by way of example and by way of preference: cyclopropyl, cyclobutyl, cyclopentyl and cyclohexyl.

For the purposes of the invention, $(C_1-C_6)$-alkoxy, $(C_1-C_4)$-alkoxy and $(C_1-C_3)$-alkoxy represent a straight-chain or branched alkoxy radical having 1 to 6, 1 to 4 and 1 to 3 carbon atoms, respectively. Preference is given to a straight-chain or branched alkoxy radical having 1 to 4, particularly preferably 1 to 3, carbon atoms. The following radicals may be mentioned by way of example and by way of preference: methoxy, ethoxy, n-propoxy, isopropoxy, n-butoxy, tert-butoxy, n-pentoxy and n-hexoxy.

For the purposes of the invention, $(C_1-C_6)$-alkoxycarbonyl and $(C_1-C_4)$-alkoxycarbonyl represent a straight-chain or branched alkoxy radical having 1 to 6 and 1 to 4 carbon atoms, respectively, which is attached via a carbonyl group. Preference is given to a straight-chain or branched alkoxycarbonyl radical having 1 to 4 carbon atoms in the alkoxy group. The following radicals may be mentioned by way of example and by way of preference: methoxycarbonyl, ethoxycarbonyl, n-propoxycarbonyl, isopropoxycarbonyl and tert-butoxycarbonyl.

For the purposes of the invention, mono-$(C_1-C_6)$-alkylamino, mono-$(C_1-C_4)$-alkylamino and mono-$(C_1-C_3)$-alkylamino represent an amino group having a straight-chain or branched alkyl substituent which has 1 to 6, 1 to 4 and 1 to 3 carbon atoms, respectively. Preference is given to a straight-chain or branched monoalkylamino radical having 1 to 4, particularly preferably 1 to 3, carbon atoms. The following radicals may be mentioned by way of example and by way of preference: methylamino, ethylamino, n-propylamino, isopropylamino, n-butylamino, tert-butylamino, n-pentylamino and n-hexylamino.

For the purposes of the invention, mono-$(C_2-C_6)$-alkenylamino represents an amino group having a straight-chain or branched alkenyl substituent having 2 to 6 carbon atoms. Preference is given to a straight-chain or branched monoalkenylamino radical having 1 to 4 carbon atoms. The following radicals may be mentioned by way of example and by way of preference: allylamino, 1-methylprop-2-en-1-ylamino, 2-methylprop-2-en-1-ylamino, but-2-en-1-ylamino and but-3-en-1-ylamino.

For the purposes of the invention, di-$(C_1-C_6)$-alkylamino, di-$(C_1-C_4)$-alkylamino and di-$(C_1-C_3)$ alkylamino represent an amino group having two identical or different straight-chain or branched alkyl substituents having 1 to 6, 1 to 4 and 1 to 3 carbon atoms each, respectively. Preference is given to straight-chain or branched dialkylamino radicals having in each case 1 to 4, particularly preferably in each case 1 to 3, carbon atoms. The following radicals may be mentioned by way of example and by way of preference: N,N-dimethylamino, N,N-diethylamino, N-ethyl-N-methylamino, N-methyl-N-n-propylamino, N-isopropyl-N-n-propylamino, N,N-diisopropylamino, N-n-butyl-N-methylamino, N-tert-butyl-N-methylamino, N-ethyl-N-n-pentylamino and N-n-hexyl-N-methylamino.

For the purposes of the invention, mono- and di-$(C_1-C_6)$-alkylaminocarbonyl represent an amino group which is attached via a carbonyl group and which has a straight-chain or branched or two identical or different straight-chain or branched alkyl substituents having in each case 1 to 6 carbon atoms. Preference is given to a mono- or dialkylaminocarbonyl radical having 1 to 4 carbon atoms in the alkyl group. The following radicals may be mentioned by way of example and by way of preference: methylaminocarbonyl, ethylaminocarbonyl, n-propylaminocarbonyl, isopropyl-aminocarbonyl, n-butylaminocarbonyl, tert-butylaminocarbonyl, N,N-dimethylaminocarbonyl, N,N-diethylaminocarbonyl, N-ethyl-N-methylaminocarbonyl, N-methyl-N-n-propylaminocarbonyl, N-n-butyl-N-methylaminocarbonyl and N-tert-butyl-N-methylaminocarbonyl.

For the purposes of the invention, $(C_6-C_{10})$-aryl represents an aromatic carbocycle having 6 or 10 ring carbon atoms. Preferred aryl radicals are phenyl and naphthyl.

For the purposes of the invention, a 4- to 7-membered heterocycle represents a saturated heterocycle having a total of 4 to 7 ring atoms which contains one or two ring heteroatoms from the group consisting of N, O and S and which is attached via a ring carbon atom or, if appropriate, via a ring nitrogen atom. Preference is given to a 5- or 6-membered heterocycle having one or two ring heteroatoms from the group consisting of N and O. The following radicals may be mentioned by way of example: azetidinyl, oxetanyl, pyrrolidinyl, pyrazolidinyl, tetrahydrofuranyl, piperidinyl, piperazinyl, tetrahydropyranyl, morpholinyl, thiomorpholinyl, hexahydroazepinyl and hexahydro-1,4-diazepinyl. Preference is given to pyrrolidinyl, tetrahydrofuranyl, piperidinyl, piperazinyl, tetrahydropyranyl and morpholinyl.

For the purposes of the invention, 5- to 10-membered heteroaryl represents a mono- or, if appropriate, bicyclic aromatic heterocycle (heteroaromatic) having a total of 5 to 10 ring atoms which contains up to three identical or different ring heteroatoms from the group consisting of N, O and S and which is attached via a ring carbon atom, or, if appropriate, via a ring nitrogen atom. The following radicals may be mentioned by way of example: furyl, pyrrolyl, thienyl, pyrazolyl, imidazolyl, thiazolyl, oxazolyl, isoxazolyl, isothiazolyl, triazolyl, oxadiazolyl, thiadiazolyl, pyridyl, pyrimidinyl, pyridazinyl, pyrazinyl, triazinyl, benzofuranyl, benzothienyl, benzimidazolyl, benzoxazolyl, benzothiazolyl, benzotriazolyl, indolyl, indazolyl, quinolinyl, isoquinolinyl, naphthyridinyl, quinazolinyl, quinoxalinyl, phthalazinyl, pyrazolo[3,4-b]pyridinyl. Preference is given to monocyclic 5- or 6-membered heteroaryl radicals having up to three ring heteroatoms from the group consisting of N, O and S, such as, for example, furyl, thienyl, thiazolyl, oxazolyl, isothiazolyl, isoxazolyl, pyrazolyl, imidazolyl, triazolyl, oxadiazolyl, thiadiazolyl, pyridyl, pyrimidinyl, pyridazinyl, pyrazinyl, triazinyl.

For the purposes of the invention, halogen includes fluorine, chlorine, bromine and iodine. Preference is given to chlorine and fluorine.

When radicals in the compounds according to the invention are substituted, the radicals may be mono- or polysubstituted, unless specified otherwise. For the purposes of the present invention, the meanings of all radicals which occur more than once are independent of one another. Preference is given to substitution by one, two or three identical or different substituents. Very particularly preferred is substitution by one or two identical or different substituents.

Of particular importance in the context of the present invention are compounds of the formula (I) in which $R^1$ represents phenyl or 5- or 6-membered heteroaryl having up to three ring heteroatoms from the group consisting of N, O and S, each of which radicals is
  (i) mono- or disubstituted by identical or different radicals selected from the group consisting of halogen, nitro, cyano, $(C_1-C_6)$-alkyl, trifluoromethyl, hydroxyl, $(C_1-C_6)$-alkoxy, amino, mono-$(C_1-C_6)$-alkylamino, di-$(C_1-C_6)$-alkylamino, mono-$(C_2-C_6)$-alkenylamino, carboxyl, $(C_1-C_6)$-alkoxycarbonyl, carbamoyl, mono-$(C_1-C_6)$-alkylaminocarbonyl and di-$(C_1-C_6)$-alkylaminocarbonyl
  and/or
  (ii) substituted by pyrrolidino, piperidino, morpholino, piperazino, N'-$(C_1-C_4)$-alkylpiperazino, or a group of the formula -L-$R^3$ in which
    L represents a bond, NH or O
    and
    $R^3$ represents phenyl or 5- or 6-membered heteroaryl having up to three ring heteroatoms from the group consisting of N, O and S, each of which radicals may be mono- to trisubstituted by identical or different radicals selected from the group consisting of halogen, nitro, cyano, $(C_1-C_6)$-alkyl, trifluoromethyl, hydroxyl, $(C_1-C_6)$-alkoxy, difluoromethoxy, trifluoromethoxy, amino, mono-$(C_1-C_6)$-alkylamino, di-$(C_1-C_6)$-alkylamino, $(C_1-C_6)$-alkoxycarbonyl and carboxyl,
or
$R^1$ represents N-oxidopyridyl,
and salts, solvates and solvates of the salts thereof.

In the context of the present invention, preference is given to compounds of the formula (I) in which ring A represents a 5- to 7-membered heterocycle which is attached via nitrogen and which may contain a further ring heteroatom from the group consisting of N and O and which may be
  (i) substituted up to five times by identical or different substituents from the group consisting of $(C_1-C_3)$-alkyl which for its part may be mono- or disubstituted by identical or different substituents from the group consisting of oxo, hydroxyl, $(C_1-C_3)$-alkoxy, amino, mono-$(C_1-C_3)$-alkylamino, di-$(C_1-C_3)$-alkylamino and $(C_3-C_5)$-cycloalkyl,
  and/or
  (ii) mono- or disubstituted by identical or different radicals selected from the group consisting of oxo, hydroxyl, $(C_1-C_3)$-alkoxy, amino, mono-$(C_1-C_3)$-alkylamino, di-$(C_1-C_3)$-alkylamino and $(C_3-C_5)$-cycloalkyl,
$R^1$ represents phenyl or 5- or 6-membered heteroaryl having up to three ring heteroatoms from the group consisting of N, O and S, each of which radicals is
  (i) mono- or disubstituted by identical or different radicals selected from the group consisting of fluorine, chlorine, cyano, $(C_1-C_4)$-alkyl, amino, mono-$(C_1-C_4)$-alkylamino and di-$(C_1-C_4)$-alkylamino
  and/or
  (ii) substituted by morpholino, N'-$(C_1-C_4)$-alkylpiperazino or a group of the formula -L-$R^3$ in which
    L represents a bond or NH
    and
    $R^3$ represents phenyl or 5- or 6-membered heteroaryl having up to three ring heteroatoms from the group consisting of N, O and S, each of which radicals may be mono- to trisubstituted by identical or different radicals selected from the group consisting of fluorine, chlorine, cyano, $(C_1-C_4)$-alkyl, trifluoromethyl, $(C_1-C_4)$-alkoxy, trifluoromethoxy and carboxyl,
or
$R^1$ represents N-oxidopyridyl,
and
$R^2$ represents hydrogen or represents $(C_1-C_4)$-alkoxy which may be substituted up to three times by fluorine
or
$R^2$ represents a group of the formula —$NR^4R^5$ in which
  $R^4$ represents hydrogen or $(C_1-C_4)$-alkyl which may be substituted by hydroxyl, $(C_1-C_4)$-alkoxy, amino, mono- ($C_1$-$C_4$)-alkylamino, di-($C_1$-$C_4$)-alkylamino, carboxyl, ($C_1$-$C_4$)-alkoxycarbonyl or a 5- or 6-membered heterocycle,
where the heterocycle mentioned contains one or two ring heteroatoms from the group consisting of N and O and for its part may be mono- or disubstituted by identical or different radicals from the group consisting of methyl, ethyl, hydroxyl, methoxy and ethoxy,
$R^5$ represents hydrogen or methyl
or
$R^4$ and $R^5$ together with the nitrogen atom, to which they are attached, form a 5- or 6-membered heterocycle which may contain a further ring heteroatom from the group consisting of N or O and may be mono- or disubstituted by identical or different radicals from the group consisting of methyl, ethyl, hydroxyl, methoxy and ethoxy,
and salts, solvates and solvates of the salts thereof.

In the context of the present, invention, particular preference is given to compounds of the formula (I) in which ring A represents a group of the formula

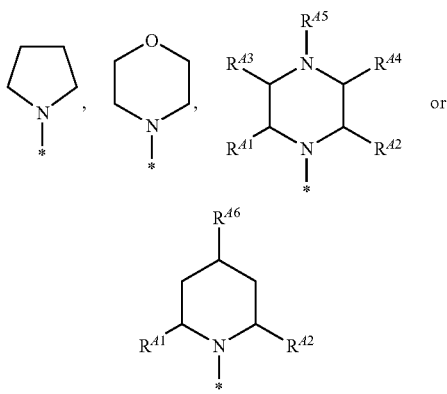

in which
* denotes the point of attachment to the pyridine ring,
$R^{A1}$, $R^{A2}$, $R^{A3}$ and, $R^{A4}$ independently of one another represent hydrogen or methyl,
$R^{A5}$ represents hydrogen, methyl, ethyl, 2-hydroxyethyl or cyclopropylmethyl
and
$R^{A6}$ represents hydrogen, methyl, ethyl, cyclopropylmethyl, hydroxymethyl, 2-hydroxyethyl, hydroxyl, methoxy or ethoxy,
$R^1$ represents phenyl, oxazolyl, thiazolyl or pyridyl, each of which radicals is
(i) mono- or disubstituted by identical or different radicals selected from the group consisting of fluorine, chlorine, methyl and amino
or
(ii) substituted by a group of the formula -L-$R^3$ in which
L represents a bond or NH
and
$R^3$ represents phenyl or pyridyl, each of which radicals may be mono- or disubstituted by identical or different radicals selected from the group consisting of fluorine, chlorine, cyano, methyl and methoxy,
or
$R^1$ represents N-oxidopyridyl,
and
$R^2$ represents hydrogen, methoxy or a group of the formula —$NR^4R^5$ in which $R^4$ represents hydrogen or ($C_1$-$C_4$)-alkyl which may be substituted by hydroxyl, amino, methylamino, ethylamino, dimethylamino or diethylamino,
$R^5$ represents hydrogen
or
$R^4$ and $R^5$ together with the nitrogen atom to which they are attached form a group of the formula

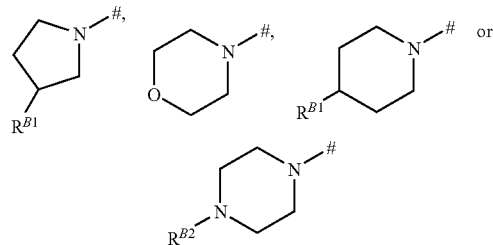

in which
# denotes the point of attachment to the pyridine ring,
$R^{B1}$ represents hydrogen or hydroxyl
and
$R^{B2}$ represents hydrogen or methyl,
and salts, solvates and solvates of the salts thereof.

The present invention furthermore provides a process for preparing the compounds of the formula (I) according to the invention in which $R^2$ represents $NH_2$, characterized in that the compound of the formula (II)

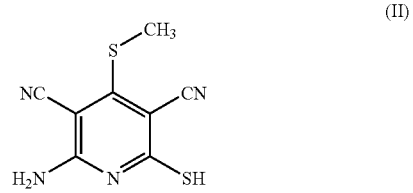

(II)

is initially, in an inert solvent in the presence of a base, reacted with a compound of the formula (III)

(III)

in which $R^1$ has the meaning given above and
X represents a suitable leaving group, preferably halogen, in particular chlorine, bromine or iodine, or represents mesylate, tosylate or triflate,
to give a compound of the formula (IV)

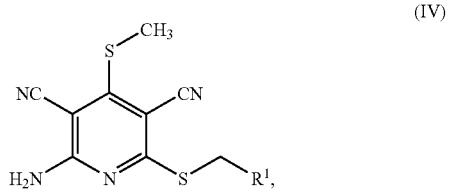

(IV)

in which $R^1$ has the meaning given above,
and this compound is then, in an inert solvent or without further solvent, reacted with a compound of the formula (V)

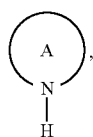
(V)

in which ring A has the meaning given above,
to give a compound of the formula (I-A)

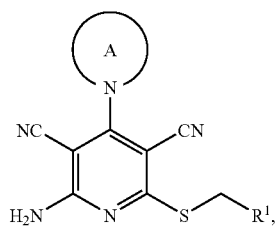
(I-A)

in which $R^1$ and ring A have the meanings given above,
and the compounds of the formula (I-A) are, if appropriate, converted with the appropriate (i) solvents and/or (ii) bases or acids into their solvates, salts and/or solvates of the salts.

The process described above can be illustrated by the reaction scheme below:

Scheme 1

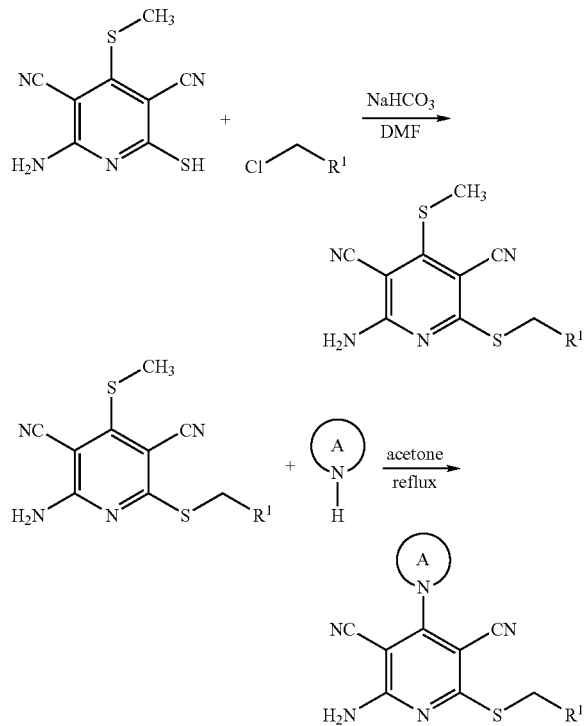

[for the second reaction step cf. also D. Briel et. al., *J. Chem. Res. Miniprint* 7, 1841-1859 (1991)].

Solvents suitable for the process step (II)+(III)→(IV) are all organic solvents which are inert under the reaction conditions. These include alcohols, such as methanol, ethanol, n-propanol, isopropanol, n-butanol and tert-butanol, ketones, such as acetone and methyl ethyl ketone, acyclic and cyclic ethers, such as diethyl ether, methyl tert-butyl ether, 1,2-dimethoxyethane, tetrahydrofuran and dioxane, esters, such as ethyl acetate or butyl acetate, hydrocarbons, such as benzene, toluene, xylene, hexane and cyclohexane, chlorinated hydrocarbons, such as dichloromethane, trichloromethane and chlorobenzene, or other solvents, such as dimethyl-formamide (DMF), dimethyl sulfoxide (DMSO), N-methylpyrrolidinone (NMP), acetonitrile or pyridine. Another suitable solvent is water. It is also possible to use mixtures of the solvents mentioned above. Preferred for use as solvent is dimethylformamide.

Bases suitable for the process step (II)+(III)→(IV) are the customary inorganic or organic bases. These preferably include alkali metal hydroxides, such as, for example, lithium hydroxide, sodium hydroxide or potassium hydroxide, alkali metal carbonates, such as lithium carbonate, sodium carbonate, potassium carbonate or cesium carbonate, alkali metal bicarbonates, such as sodium bicarbonate or potassium bicarbonate, alkali metal alkoxides, such as sodium methoxide or potassium methoxide, sodium ethoxide or potassium ethoxide or potassium tert-butoxide, amides, such as sodium amide, lithium bis(trimethylsilyl)amide, sodium bis(trimethylsilyl)amide or potassium bis(trimethylsilyl)amide or lithium diisopropylamide, organometallic compounds, such as butyllithium or phenyllithium, or organic amines, such as triethylamine, diisopropylethylamine, pyridine, 1,8-diazabicyclo[5.4.0]undec-7-ene (DBU) or 1,5-diazabicyclo[4.3.0]non-5-ene (DBN).

Preference is given to alkali metal carbonates and alkali metal bicarbonates.

Here, the base can be employed in an amount of from 1 to 10 mol, preferably from 1 to 5 mol, in particular from 1 to 4 mol, per mole of the compound of the formula (II).

In general, the reaction is carried out in a temperature range of from −78° C. to +140° C., preferably in the range of from −20° C. to +80° C., in particular at from 0° C. to +50° C. The reaction can be carried out at atmospheric, elevated or reduced pressure (for example in the range of from 0.5 to 5 bar). In general, the reaction is carried out at atmospheric pressure.

Solvents suitable for the process step (IV)+(V)→(I-A) are all organic solvents which are inert under the reaction conditions. These include alcohols, such as methanol, ethanol, n-propanol, isopropanol, n-butanol and tert-butanol, ketones, such as acetone and methyl ethyl ketone, acyclic and cyclic ethers, such as diethyl ether, methyl tert-butyl ether, 1,2-dimethoxyethane, tetrahydrofuran and dioxane, esters, such as ethyl acetate or butyl acetate, hydrocarbons, such as benzene, toluene, xylene, hexane and cyclohexane, chlorinated hydrocarbons, such as dichloromethane chlorobenzene, or other solvents, such as dimethylformamide (DMF), dimethyl sulfoxide (DMSO), N-methylpyrrolidinone (NMP), acetonitrile or pyridine. Another suitable solvent is water. It is also possible to use mixtures of the solvents mentioned above. If appropriate, the reaction can also be carried out in an advantageous manner in the presence of an excess of the compound (V) without addition of a further solvent. Preferably, the reaction is carried out in the solvent acetone or N-methylpyrrolidinone.

The process step (IV)+(V)→(I-A) is generally carried out in a temperature range of from 0° C. to +180° C., preferably in the range of from +20° C. to +100° C., in particular at from +60° C. to +100° C. The reaction can be carried out at atmospheric, elevated or reduced pressure (for example in the range of from 0.5 to 5 bar). In general, the reaction is carried out at atmospheric pressure.

The compound of the formula (II) can be obtained in a simple manner by reacting [bis(methylthio)-methylene]malononitrile with cyanothioacetamide in the presence of a base such as triethylamine.

This process can be illustrated by the reaction scheme below:

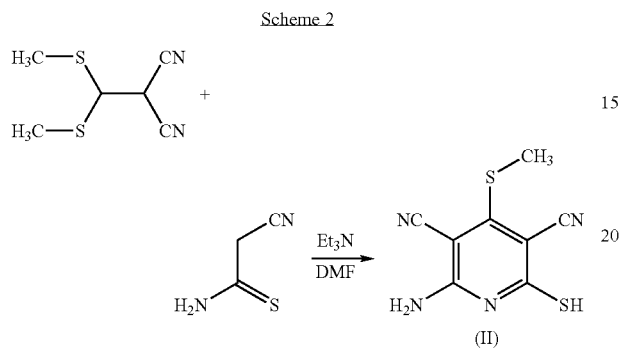

The compounds of the formula (III) are commercially available, known from the literature or can be prepared by methods known from the literature. Thus, for example, substituted oxazole and thiazole derivatives of the formulae (III-A), (III-B) and (III-C) are obtained by reacting amides, thioamides and thiourea derivatives, respectively, with a 1,3-dihaloacetone (see Scheme 3):

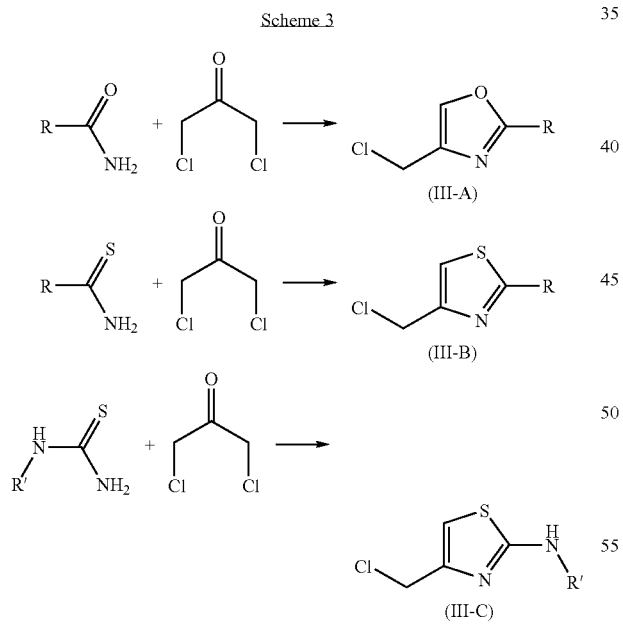

In the case of the compounds (III-C), these can either be prepared and isolated analogously to the literature [cf., for example, I. Simiti et al., Chem. Ber. 95, 2672-2679 (1962)], or they can be generated in situ and directly reacted further with a compound of the formula (II). Preference is given to the in situ generation using 1,3-dichloroacetone in dimethylformamide or ethanol as solvent. The preparation is generally carried out in a temperature range of from 0° C. to +140° C., preferably in the range of from +20° C. to +120° C., in particular at from +60° C. to +100° C.

The compounds of the formula (V) are likewise commercially available, have been described in the literature or can be prepared by standard methods [see, for example. A. Ladenburg, *Justus Liebigs Ann. Chem.* 247, 1-98 (1888); H. Nienburg, *Chem. Ber.* 70, 635-638 (1937); E. Koenigs, L. Neumann, *Chem. Ber.* 48, 956-963 (1915)].

The compounds of the formula (I) according to the invention in which $R^2$ represents the group $-NR^4R^5$ and in which at least one of the two radicals $R^4$ and $R^5$ is not hydrogen can be prepared by converting compounds of the formula (I-A) initially with copper(II) chloride and isoamyl nitrite in a suitable solvent into compounds of the formula (VI)

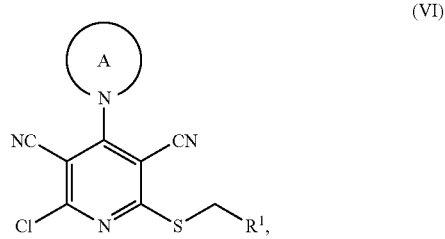

(VI)

in which $R^1$ and ring A have the meanings given above, and these are then reacted with a compound of the formula (VII)

(VII)

in which $R^{4A}$ has the meaning of $R^4$ given above, $R^{5A}$ has the meaning of $R^5$ given above, but at least one of the two radicals $R^{4A}$ and $R^{5A}$ does not represent hydrogen, to give compounds of the formula (I-B)

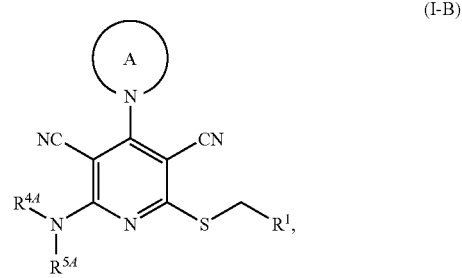

(I-B)

in which $R^1$, $R^{4A}$, $R^{5A}$ and ring A each have the meanings given above.

The process described above can be illustrated by the reaction scheme below:

Scheme 4

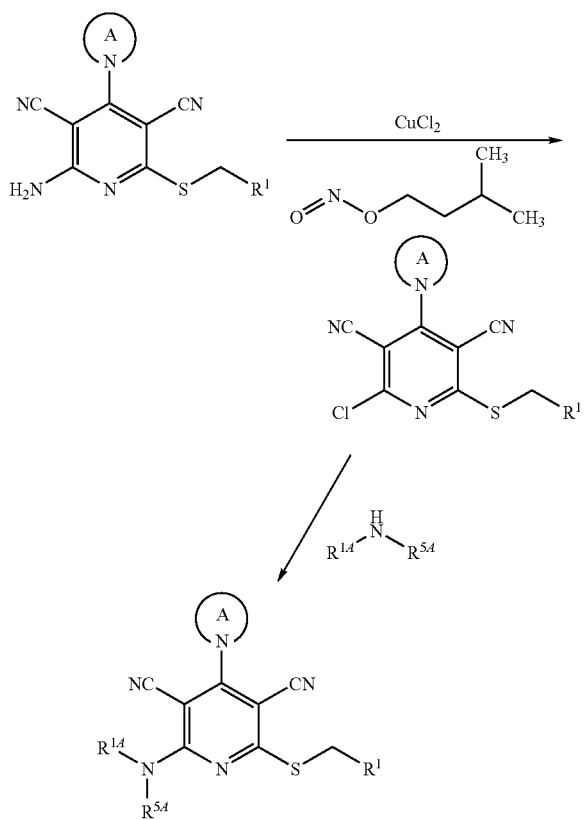

The reaction (I-A)→(VI) is generally carried out in a molar ratio of from 2 to 12 mol of copper(II) chloride and 2 to 12 mol of isoamyl nitrite per mole of the compound of the formula (I-A).

Solvents suitable for the process step (I-A)→(VI) are all organic solvents which are inert under the reaction conditions. These include acyclic and cyclic ethers, such as diethyl ether and tetrahydrofuran, esters, such as ethyl acetate or butyl acetate, hydrocarbons, such as benzene, toluene, xylene, hexane and cyclohexane, chlorinated hydrocarbons, such as dichloromethane, 1,2-dichloroethane and chlorobenzene, or other solvents, such as dimethylformamide, acetonitrile or pyridine. It is also possible to use mixtures of the solvents mentioned above. Preferred solvents are acetonitrile and dimethylformamide.

In general, the reaction is carried out in a temperature range of from −78° C. to +180° C., preferably in the range of from 0° C. to +100° C., in particular at from +20° C. to +80° C. The reaction can be carried out at atmospheric, elevated or reduced pressure (for example in the range of from 0.5 to 5 bar). In general, the reaction is carried out at atmospheric pressure.

The reaction (VI)+(VII)→(I-B) is generally carried out using a molar ratio of from 1 to 8 mol of the compound of the formula (VII) per mole of the compound of the formula (VI).

Solvents suitable for the process step (VI)+(VII)→(I-B) are all organic solvents which are inert under the reaction conditions. These include alcohols, such as methanol, ethanol, n-propanol, iso-propanol, n-butanol and tert-butanol, ketones, such as acetone and methyl ethyl ketone, acyclic and cyclic ethers, such as diethyl ether, 1,2-dimethoxyethane, tetrahydrofuran and dioxane, esters, such as ethyl acetate or butyl acetate, hydrocarbons, such as benzene, toluene, xylene, hexane and cyclohexane, chlorinated hydrocarbons, such as dichloromethane, 1,2-dichloroethane and chlorobenzene, or other solvents, such as dimethylformamide, acetonitrile, pyridine or dimethyl sulfoxide. Another suitable solvent is water. It is also possible to use mixtures of the solvents mentioned above. The preferred solvent is dimethylformamide.

In general, the reaction is carried out in a temperature range of from 0° C. to +180° C., preferably in the range of from +20° C. to +150° C., in particular at from +20° C. to +100° C. The reaction can be carried out at atmospheric, elevated or reduced pressure (for example in the range of from 0.5 to 5 bar). In general, the reaction is carried out at atmospheric pressure.

The compounds of the formula (VII) are either commercially available, known to the person skilled in the art or can be prepared by customary methods.

The compounds of the formula (I) according to the invention in which $R^2$ represents hydrogen can be prepared by reacting compounds of the formula (I-A) in a suitable solvent with isoamyl nitrite in the presence of a catalytic amount of copper(II) chloride. This method can be illustrated by the reaction scheme below:

Scheme 5

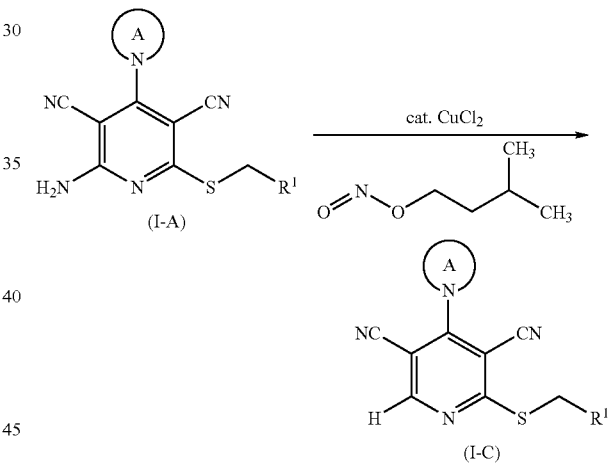

The reaction (I-A)→(I-C) is generally carried out in a molar ratio of from 0.01 to 0.2 mol of copper(II) chloride and from 2 to 12 mol of isoamyl nitrite per mole of the compound of the formula (I-A).

Solvents suitable for the reaction (I-A)→(I-C) are all organic solvents which are inert under the reaction conditions. These include acyclic and cyclic ethers, such as diethyl ether and tetrahydrofuran, esters, such as ethyl acetate or butyl acetate, hydrocarbons, such as benzene, toluene, xylene, hexane and cyclohexane, chlorinated hydrocarbons, such as dichloromethane, 1,2-dichloroethane and chlorobenzene, or other solvents, such as dimethylformamide, acetonitrile or pyridine. It is also possible to use mixtures of the solvents mentioned. Preferred solvents are tetrahydrofuran and dimethylformamide.

The reaction is generally carried out in a temperature range of from −78° C. to +150° C., preferably in the range of from 0° C. to +80° C., in particular at from +10° C. to +40° C. The reaction can be carried out at atmospheric, elevated or reduced pressure (for example in the range of from 0.5 to 5 bar). In general, the reaction is carried out at atmospheric pressure.

The compounds of the formula (I) according to the invention in which $R^2$ represents optionally substituted $(C_1-C_6)$-alkyl or $(C_1-C_6)$-alkoxy can be prepared analogously to methods described in the literature from compounds of the formula (VI) [cf., for example, D. Mabire et al., *J. Med. Chem.* 48, 2134-2153 (2005)]. Alternatively, the compounds of the formula (I) in which $R^2$ represents optionally substituted $(C_1-C_6)$-alkoxy can also be obtained by alkylation of compounds of the formula (VIII) (see Scheme 6):

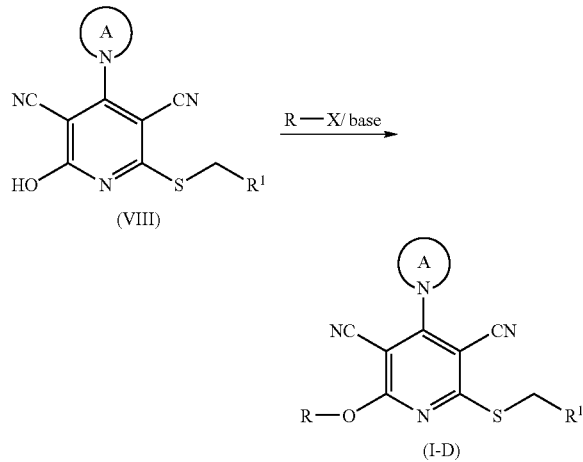

Scheme 6

For their part, the compounds of the formula (VIII) can be obtained by methods known from the literature from compounds of the formula (VI) or (I-A) [cf., for example, G. Lavecchia et al., *Tetrahedron Lett.* 45, 6633-6636 (2004)].

Surprisingly, the compounds according to the invention have an unforeseeable useful pharmacological activity spectrum and are therefore particularly suitable for the prophylaxis and/or treatment of disorders. In addition, the substances according to the invention have, compared to the compounds of the prior art, an improved resorption bevavior in the body and/or improved solubility in water and other physiological media, which is advantageous, for example, for their ease of galenic formulation and/or parenteral administration.

The pharmacological activity of the compounds according to the invention can be explained by their action as potent, selective ligands at adenosine A1 and/or A2b receptors. Here, they act as selective A1 agonists or as selective dual A1/A2b agonists.

In the context of the present invention, "selective ligands at adenosine A1 and/or A2b receptors" are adenosine receptor ligands where firstly a marked activity at A1 and/or A2b adenosine receptor subtypes and secondly no or a considerably weaker activity (by a factor of 10 or more) at A2a and A3 adenosine receptor subtypes can be observed, where with respect to the test methods for activity/selectivity, reference is made to the tests described in section B-1.

The compounds of the formula (I), on their own or in combination with one or more other active compounds, are suitable for the prophylaxis and/or treatment of various disorders such as, for example, in particular hypertension and other disorders of the cardiovascular system (cardiovascular disorders), and for cardioprotection.

In the context of the present invention, disorders of the cardiovascular system or cardiovascular disorders are to be understood as including, in addition to hypertension, for example in particular the following disorders: peripheral and cardial vascular disorders, coronary heart disease, coronary restenosis, such as, for example, restenosis after balloon dilation of peripheral blood vessels, acute coronary syndrome, stable and unstable angina pectoris, heart failure, tachycardias, arrhythmias, atrial and ventricular fibrillation and impaired peripheral circulation.

The compounds according to the invention are furthermore also particularly suitable for reducing the myocard region affected by an infarct, and also for the prophylaxis of secondary infarcts.

Furthermore, compounds according to the invention are particularly suitable for the prophylaxis and/or treatment of thromboembolic disorders and ischemias, such as myocardial infarction, stroke and transitory ischemic attacks, and also for organ protection during transplantations and surgical interventions, for example on the heart.

Further indications for which the compounds according to the invention may be used are, for example, the prophylaxis and/or treatment of disorders of the urogenital system, such as, for example, in irritable bladder, erectile dysfunction and female sexual dysfunction, but in addition also the prophylaxis and/or treatment of inflammatory disorders, such as, for example, asthma and inflammatory dermatoses, of neuroinflammatory disorders of the central nervous system such as, for example, conditions following stroke, Alzheimer's disease and furthermore of neurodegenerative disorders, and also of pain, neoplastic diseases and nausea and emesis associated with cancer therapies.

A further indication is, for example, the prophylaxis and/or treatment of disorders of the respiratory tract, such as, for example, asthma, chronic bronchitis, pulmonary emphysema, bronchiectasias, cystic fibrosis (mucoviscidosis) and pulmonary hypertension.

Finally, the compounds according to the invention are also suitable for the prophylaxis and/or treatment of diabetes, in particular diabetes mellitus, diabetic sequelae, such as, for example, nephropathy and neuropathy, metabolic syndrome and also dyslipidemias.

The present invention furthermore provides the use of the compounds according to the invention for the treatment and/or prophylaxis of disorders, in particular the disorders mentioned above.

The present invention also provides the use of the compounds according to the invention for preparing a medicament for the treatment and/or prophylaxis of disorders, in particular the disorders mentioned above.

The present invention also provides a method for the treatment and/or prophylaxis of disorders, in particular the disorders mentioned above, using an effective amount of at least one compound according to the invention.

The compounds according to the invention can be used alone or, if required, in combination with other active compounds. The present invention furthermore provides medicaments comprising at least one compound according to the invention and one or more further active compounds, in particular for the treatment and/or prophylaxis of the disorders mentioned above.

Suitable active compounds for combinations are, by way of example and by way of preference: active compounds which modulate lipid metabolism, antidiabetics, hypotensive agents, perfusion-enhancing and/or antithrombotic agents, antioxidants, chemokine receptor antagonists, p38-kinase inhibitors, NPY agonists, orexin agonists, anorectics, PAF-AH inhibitors, antiphlogistics (COX inhibitors, LTB$_4$-receptor antagonists) and analgesics such as, for example, aspirin.

The present invention provides in particular combinations comprising at least one of the compounds according to the invention and at least one lipid metabolism-modulating active compound, an antidiabetic, a hypotensive active compound and/or an antithrombotic agent.

Preferably, the compounds according to the invention can be combined with one or more lipid metabolism-modulating active compounds, by way of example and by way of preference from the group of the HMG-CoA reductase inhibitors, inhibitors of HMG-CoA reductase expression, squalene synthesis inhibitors, ACAT inhibitors, LDL receptor inductors, cholesterol absorption inhibitors, polymeric bile acid adsorbers, bile acid reabsorption inhibitors, MTP inhibitors, lipase inhibitors, LpL activators, fibrates, niacin, CETP inhibitors, PPAR-α, PPAR-γ and/or PPAR-δ agonists, RXR modulators, FXR modulators, LXR modulators, thyroid hormones and/or thyroid mimetics, ATP citrate lyase inhibitors, Lp(a) antagonists, cannabinoid receptor 1 antagonists, leptin receptor agonists, bombesin receptor agonists, histamine receptor agonists and the antioxidants/radical scavengers;

antidiabetics mentioned in the Rote Liste 2004/II, chapter 12, and also, by way of example and by way of preference, those from the group of the sulfonylureas, biguanides, meglitinide derivatives, glucosidase inhibitors, oxadiazolidinones, thiazolidinediones, GLP 1 receptor agonists, glucagon antagonists, insulin sensitizers, CCK 1 receptor agonists, leptin receptor agonists, inhibitors of liver enzymes involved in the stimulation of gluconeogenesis and/or glycogenolysis, modulators of glucose uptake and also potassium channel openers, such as, for example, those disclosed in WO 97/26265 and WO 99/03861;

hypotensive active compounds, by way of example and by way of preference from the group of the calcium antagonists, angiotensin AII antagonists, ACE inhibitors, renin inhibitors, beta-receptor blockers, alpha-receptor blockers, diuretics, phosphodiesterase inhibitors, sGC stimulators, substances which increase the cGMP concentration, aldosterone antagonists, mineralocorticoid receptor antagonists, ECE inhibitors and the vasopeptidase inhibitors; and/or antithrombotic agents, by way of example and by way of preference from the group of the platelet aggregation inhibitors or the anticoagulants.

Lipid metabolism-modifying active compounds are to be understood as meaning, preferably, compounds from the group of the HMG-CoA reductase inhibitors, squalene synthesis inhibitors, ACAT inhibitors, cholesterol absorption inhibitors, MTP inhibitors, lipase inhibitors, thyroid hormones and/or thyroid mimetics, niacin receptor agonists, CETP inhibitors, PPAR-α agonists PPAR-γ agonists, PPAR-δ agonists, polymeric bile acid adsorbers, bile acid reabsorption inhibitors, antioxidants/radical scavengers and also the cannabinoid receptor 1 antagonists.

In a preferred embodiment of the invention, the compounds according to the invention are administered in combination with an HMG-CoA reductase inhibitor from the class of the statins, such as, by way of example and by way of preference, lovastatin, simvastatin, pravastatin, fluvastatin, atorvastatin, rosuvastatin, cerivastatin or pitavastatin.

In a preferred embodiment of the invention, the compounds according to the invention are administered in combination with a squalene synthesis inhibitor, such as, by way of example and by way of preference, BMS-188494 or TAK-475.

In a preferred embodiment of the invention, the compounds according to the invention are administered in combination with an ACAT inhibitor, such as, by way of example and by way of preference, avasimibe, melinamide, pactimibe, eflucimibe or SMP-797.

In a preferred embodiment of the invention, the compounds according to the invention are administered in combination with a cholesterol absorption inhibitor, such as, by way of example and by way of preference, ezetimibe, tiqueside or pamaqueside.

In a preferred embodiment of the invention, the compounds according to the invention are administered in combination with an MTP inhibitor, such as, by way of example and by way of preference, implitapide, BMS-201038, R-103757 or JTT-130.

In a preferred embodiment of the invention, the compounds according to the invention are administered in combination with a lipase inhibitor, such as, by way of example and by way of preference, orlistat.

In a preferred embodiment of the invention, the compounds according to the invention are administered in combination with a thyroid hormone and/or thyroid mimetic, such as, by way of example and by way of preference, D-thyroxine or 3,5,3'-triiodothyronine (T3).

In a preferred embodiment of the invention, the compounds according to the invention are administered in combination with an agonist of the niacin receptor, such as, by way of example and by way of preference, niacin, acipimox, acifran or radecol.

In a preferred embodiment of the invention, the compounds according to the invention are administered in combination with a CETP inhibitor, such as, by way of example and by way of preference, torcetrapib, JTT-705, BAY 60-5521, BAY 78-7499 or CETP vaccine (Avant).

In a preferred embodiment of the invention, the compounds according to the invention are administered in combination with a PPAR-γ agonist, such as, by way of example and by way of preference, pioglitazone or rosiglitazone.

In a preferred embodiment of the invention, the compounds according to the invention are administered in combination with a PPAR-δ agonist, such as, by way of example and by way of preference, GW-501516 or BAY 68-5042.

In a preferred embodiment of the invention, the compounds according to the invention are administered in combination with a polymeric bile acid adsorber, such as, by way of example and by way of preference, cholestyramine, colestipol, colesolvam, CholestaGel or colestimide.

In a preferred embodiment of the invention, the compounds according to the invention are administered in combination with a bile acid reabsorption inhibitor, such as, by way of example and by way of preference, ASBT (=IBAT) inhibitors, such as, for example, AZD-7806, S-8921, AK-105, BARI-1741, SC-435 or SC-635.

In a preferred embodiment of the invention, the compounds according to the invention are administered in combination with an antioxidant/radical scavenger, such as, by way of example and by way of preference, probucol, AGI-1067, BO-653 or AEOL-10150.

In a preferred embodiment of the invention, the compounds according to the invention are administered in combination with a cannabinoid receptor 1 antagonist, such as, by way of example and by way of preference, rimonabant or SR-147778.

Antidiabetics are to be understood as meaning, preferably, insulin and insulin derivatives, and also orally effective hypoglycemic active compounds. Here, insulin and insulin derivatives include both insulins of animal, human or biotechnological origin and also mixtures thereof. The orally effective hypoglycemic active compounds preferably include sulfonylureas, biguanides, meglitinide derivatives, glucosidase inhibitors and PPAR-γ agonists.

In a preferred embodiment of the invention, the compounds according to the invention are administered in combination with insulin.

In a preferred embodiment of the invention, the compounds according to the invention are administered in combination with a sulfonylurea, such as, by way of example and by way of preference, tolbutamide, glibenclamide, glimepiride, glipizide or gliclazide.

In a preferred embodiment of the invention, the compounds according to the invention are administered in combination with a biguanide, such as, by way of example and by way of preference, metformin In a preferred embodiment of the invention, the compounds according to the invention are administered in combination with a meglitinide derivative, such as, by way of example and by way of preference, repaglinide or nateglinide.

In a preferred embodiment of the invention, the compounds according to the invention are administered in combination with a glucosidase inhibitor, such as, by way of example and by way of preference, miglitol or acarbose.

In a preferred embodiment of the invention, the compounds according to the invention are administered in combination with a PPAR-γ agonist, for example from the class of the thiazolidinediones, such as, by way of example and by way of preference, pioglitazone or rosiglitazone.

The hypotensive agents are preferably understood as meaning compounds from the group of the calcium antagonists, angiotensin AII antagonists, ACE inhibitors, beta-receptor blockers, alpha-receptor blockers and diuretics.

In a preferred embodiment of the invention, the compounds according to the invention are administered in combination with a calcium antagonist, such as, by way of example and by way of preference, nifedipine, amlodipine, verapamil or diltiazem.

In a preferred embodiment of the invention, the compounds according to the invention are administered in combination with an angiotensin AII antagonist, such as, by way of example and by way of preference, losartan, valsartan, candesartan, embusartan, almesartan or telmisartan.

In a preferred embodiment of the invention, the compounds according to the invention are administered in combination with an ACE inhibitor, such as, by way of example and by way of preference, enalapril, captopril, lisinopril, ramipril, delapril, fosinopril, quinopril, perindopril or trandopril.

In a preferred embodiment of the invention, the compounds according to the invention are administered in combination with a beta-receptor blocker, such as, by way of example and by way of preference, propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the compounds according to the invention are administered in combination with an alpha-receptor blocker, such as, by way of example and by way of preference, prazosin.

In a preferred embodiment of the invention, the compounds according to the invention are administered in combination with a diuretic, such as, by way of example and by way of preference, furosemide, bumetanide, torsemide, bendroflumethiazide, chlorothiazide, hydrochlorothiazide, hydroflumethiazide, methyclothiazide, polythiazide, trichloromethiazide, chlorothalidone, indapamide, metolazone, quinethazone, acetazolamide, dichlorophenamide, methazolamide, glycerol, isosorbide, mannitol, amiloride or triamteren.

In a preferred embodiment of the invention, the compounds according to the invention are administered in combination with antisympathotonics, such as reserpine, clonidine or alpha-methyldopa, or in combination with potassium channel agonists, such as minoxidil, diazoxide, dihydralazine or hydralazine, or with substances which release nitrogen oxide, such as glycerol nitrate or sodium nitroprusside.

Antithrombotics are to be understood as meaning, preferably, compounds from the group of the platelet aggregation inhibitors or the anticoagulants.

In a preferred embodiment of the invention, the compounds according to the invention are administered in combination with a platelet aggregation inhibitor, such as, by way of example and by way of preference, aspirin, clopidogrel, ticlopidine or dipyridamol.

In a preferred embodiment of the invention, the compounds according to the invention are administered in combination with a thrombin inhibitor, such as, by way of example and by way of preference, ximelagatran, melagatran, bivalirudin or clexane.

In a preferred embodiment of the invention, the compounds according to the invention are administered in combination with a GPIIb/IIIa antagonist, such as, by way of example and by way of preference, tirofiban or abciximab.

In a preferred embodiment of the invention, the compounds according to the invention are administered in combination with a factor Xa inhibitor, such as, by way of example and by way of preference, rivaroxaban (BAY 59-7939), DU-176b, apixaban, otamixaban, fidexaban, razaxaban, fondaparinux, idraparinux, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the compounds according to the invention are administered in combination with heparin or a low molecular weight (LMW) heparin derivative.

In a preferred embodiment of the invention, the compounds according to the invention are administered in combination with a vitamin K antagonist, such as, by way of example and by way of preference, coumarin.

The present invention furthermore provides medicaments comprising at least one compound according to the invention, usually together with one or more inert nontoxic pharmaceutically suitable auxiliaries, and also their use for the purposes mentioned above.

The compounds according to the invention can act systemically and/or locally. For this purpose, they can be administered in a suitable manner, such as, for example, orally, parenterally, pulmonally, nasally, sublingually, lingually, buccally, rectally, dermally, transdermally, conjunctivally, otically or as an implant or stent.

For these administration routes, the compounds according to the invention can be administered in suitable administration forms.

Suitable for oral administration are administration forms which work in accordance with the prior art and release the compounds according to the invention rapidly and/or in modified form and which comprise the compounds according to the invention in crystalline and/or amorphicized and/or dissolved form, such as, for example, tablets (uncoated or coated tablets, for example with enteric coats or coats which dissolve in a delayed manner or are insoluble and which control the release of the compound according to the invention), films/wafers or tablets which dissolve rapidly in the oral cavity, films/lyophilizates, capsules (for example hard or soft gelatin capsules), sugar-coated tablets, granules, pellets, powders, emulsions, suspensions, aerosols or solutions.

Parenteral administration may take place by circumventing a bioabsorption step (for example intravenously, intraarterially, intracardially, intraspinally or intralumbarly), or with bioabsorption (for example intramuscularly, subcutaneously, intracutaneously, percutaneously or intraperitoneally). Administration forms suitable for parenteral administration are inter alia preparations for injection or infusion in the form of solutions, suspensions, emulsions, lyophilizates or sterile powders.

Suitable for other administration routes are, for example, medicaments suitable for inhalation (inter alia powder inhalers, nebulizers), nose drops, solutions or sprays, tablets to be administered lingually, sublingually or buccally, films/wafers or capsules, suppositories, preparations to be administered to ears or eyes, vaginal capsules, aqueous suspensions (lotions, shaking mixtures), lipophilic suspensions, ointments, creams, transdermal therapeutic systems (for example plasters), milk, pastes, foams, powders for pouring, implants or stents.

Preference is given to oral or parenteral administration, in particular to oral and intravenous administration.

The compounds according to the invention can be converted into the administration forms mentioned. This can be carried out in a manner known per se by mixing with inert non-toxic pharmaceutically suitable auxiliaries. These auxiliaries include inter alia carriers (for example microcrystalline cellulose, lactose, mannitol), solvents (for example liquid polyethylene glycols), emulsifiers and dispersants or wetting agents (for example sodium dodecyl sulfate, polyoxysorbitan oleate), binders (for example polyvinylpyrrolidone), synthetic and natural polymers (for example albumin), stabilizers (for example antioxidants, such as, for example, ascorbic acid), colorants (for example inorganic pigments, such as, for example, iron oxides), and flavor and/or odor corrigents.

In general, it has been found to be advantageous in the case of parenteral administration to administer amounts of about 0.001 to 1 mg/kg, preferably about 0.01 to 0.5 mg/kg of body weight to obtain effective results. In the case of oral administration, the dosage is from about 0.01 to 100 mg/kg, preferably from about 0.01 to 20 mg/kg and very particularly preferably from 0.1 to 10 mg/kg of body weight.

In spite of this, it may be necessary to deviate from the amounts mentioned, namely depending on body weight, administration route, individual response to the active compound, the type of preparation and the time or the interval at which administration takes place. Thus, in some cases it may be sufficient to administer less than the abovementioned minimum amount, whereas in other cases the upper limit mentioned has to be exceeded. In the case of the administration of relatively large amounts, it may be expedient to divide these into a plurality of individual doses which are administered over the course of the day.

The working examples below illustrate the invention. The invention is not limited to the examples.

The percentages in the tests and examples below are, unless indicated otherwise, percentages by weight; parts are parts by weight. Solvent ratios, dilution ratios and concentrations of liquid/liquid solutions are in each case based on volume.

A. EXAMPLES

Abbreviations Used

Ex. Example
TLC thin-layer chromatography
DCI direct chemical ionization (in MS)
DMF N,N-dimethylformamide
DMSO dimethyl sulfoxide
EA ethyl acetate
EI electron impact ionization (in MS)
ESI electrospray ionization (in MS)
Et ethyl
m.p. melting point
h hour(s)
HPLC high-pressure, high-performance liquid chromatography
cat. catalytic
conc. concentrated
LC-MS liquid chromatography-coupled mass spectrometry
lit. literature (reference)
min minute(s)
MS mass spectrometry
NMR nuclear magnetic resonance spectrometry
RP-HPLC reversed-phase HPLC
RT room temperature
$R_t$ retention time (in HPLC)
TFA trifluoroacetic acid
THF tetrahydrofuran
dil. dilute
aq. aqueous HPLC and LC-MS Methods:

Method 1 (HPLC):

Instrument: Hewlett Packard Series 1050; column: Symmetry TM C18 3.9×150 mm; flow rate: 1.5 ml/min; mobile phase A: water, mobile phase B: acetonitrile; gradient: →0.6 min 10% B→3.8 min 100% B→5.0 min 100% B→5.5 min 10% B; stop time: 6.0 min; injection volume: 10 µl; diode array detector signal: 214 and 254 nm.

Method 2 (LC-MS):

MS instrument type: Micromass ZQ; HPLC instrument type: Waters Alliance 2795; column: Merck Chromolith SpeedROD RP-18e 100 mm×4.6 mm; mobile phase A: water+500 µl of 50% strength formic acid/l, mobile phase B: acetonitrile+500 µl of 50% strength formic acid/l; gradient: 0.0 min 10% B→7.0 min 95% B→9.0 min 95% B; oven: 35° C.; flow rate: 0.0 min 1.0 ml/min→7.0 min 2.0 ml/min→9.0 min 2.0 ml/min; UV detection: 210 nm.

Method 3 (LC-MS):

Instrument: Micromass Quattro LCZ with HPLC Agilent Series 1100; column: Phenomenex Gemini 3μ 30 mm×3.00 mm; mobile phase A: 1 l of water+0.5 ml of 50% strength formic acid, mobile phase B: 1 l of acetonitrile+0.5 ml of 50% strength formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 208-400 nm.

Method 4 (LC-MS):

MS instrument type: Micromass ZQ; HPLC instrument type: HP 1100 Series; UV DAD; column: Phenomenex Gemini 3μ 30 mm×3.00 mm; mobile phase A: 1 l of water+0.5 ml of 50% strength formic acid, mobile phase B: 1 l of acetonitrile+0.5 ml of 50% strength formic acid; gradient: 0.0 min 90% A→2.5 min 30% A→3.0 min 5% A→4.5 min 5% A; flow rate: 0.0 min→1 ml/min 2.5 min/3.0 min/4.5 min 2 ml/min; oven: 50° C.; UV detection: 210 nm.

Method 5 (LC-MS):

Instrument: Micromass Quattro LCZ with HPLC Agilent Series 1100; column: Phenomenex Onyx Monolithic C18, 100 mm×3 mm; mobile phase A: 1 l of water+0.5 ml of 50% strength formic acid, mobile phase B: 1 l of acetonitrile+0.5 ml of 50% strength formic acid; gradient: 0.0 min 90% A→2 min 65% A→4.5 min 5% A→6 min 5% A; flow rate: 2 ml/min; oven: 40° C.; UV detection: 208-400 nm.

Method 6 (Preparative HPLC):

HPLC instrument type: Abimed/Gilson Pump 305/306; Manometric Module 806; UV Knauer Variable Wavelength Monitor; column: Gromsil C18, 10 nm, 250 mm×30 mm; mobile phase A: 1 l of water+0.5 ml 99% TFA, mobile phase B: 1 l of acetonitrile; gradient: 0.0 min 2% B→10 min 2% B→50 min 90% B; flow rate: 20 ml/min; volume: 628 ml A and 372 ml B.

Method 7 (LC-MS):

MS instrument type: Waters ZQ; HPLC instrument type: Waters Alliance 2795; column: Merck Chromolith RP18e, 100 mm×3 mm; mobile phase A: 1 l of water+0.5 ml of 50% strength formic acid, mobile phase B: 1 l of acetonitrile+0.5 ml of 50% strength formic acid; gradient: 0.0 min 90% A→2 min 65% A→4.5 min 5% A→6 min 5% A; flow rate: 2 ml/min; oven: 40° C.; UV detection: 210 nm.

Method 8 (LC-MS):

MS instrument type: Micromass ZQ; HPLC instrument type: Waters Alliance 2795; column: Phenomenex Synergi 2.5μ MAX-RP 100A Mercury, 20 mm×4 mm; mobile phase A: 1 l of water+0.5 ml of 50% strength formic acid, mobile phase B: 1 l of acetonitrile+0.5 ml of 50% strength formic acid; gradient: 0.0 min 90% A→0.1 min 90% A→3.0 min 5% A→4.0 min 5% A→4.01 min 90% A; flow rate: 2 ml/min; oven: 50° C.; UV detection: 210 nm.

Method 9 (LC-MS):

Instrument: Micromass QuattroPremier with Waters HPLC Acquity; column: Thermo Hypersil GOLD 1.9μ, 50 mm×1 mm; mobile phase A: 1 l of water+0.5 ml of 50% strength formic acid, mobile phase B: 1 l of acetonitrile+0.5 ml of 50% strength formic acid; gradient: 0.0 min 90% A→0.1 min 90% A→1.5 min 10% A→2.2 min 10% A; oven: 50° C.; flow rate: 0.33 ml/min; UV detection: 210 nm.

Starting Materials and Intermediates

Example 1A

2-Amino-6-mercapto-4-(methylthio)pyridine-3,5-dicarbonitrile

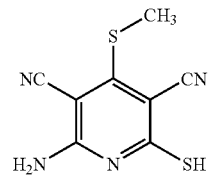

10 g (58.74 mmol) of [bis(methylthio)methylene]malononitrile and 6.5 g (64.61 mmol) of cyanothioacetamide are initially charged in 20 ml of DMF, and 16.4 ml (117.5 mmol) of triethylamine are added dropwise at room temperature. The mixture is stirred at room temperature for 8 h and allowed to stand for a further two days. The mixture is then added to 250 ml of 3 N hydrochloric acid. The resulting precipitate is filtered off with suction, washed with water and acetone and dried. This gives a yellow powder.

Yield: 12.9 g (99% of theory)

$^1$H-NMR (400 MHz, CDCl$_3$): δ=3.98 (s, 1H), 2.72 (s, 3H).

LC-MS (Method 3): R$_t$=1.43 min; MS (ESIpos): m/z=222 [M+H]$^+$.

Example 2A

2-Amino-6-({[2-(4-chlorophenyl)-1,3-thiazol-4-yl]methyl}thio)-4-(methylthio)pyridine-3,5-di-carbonitrile

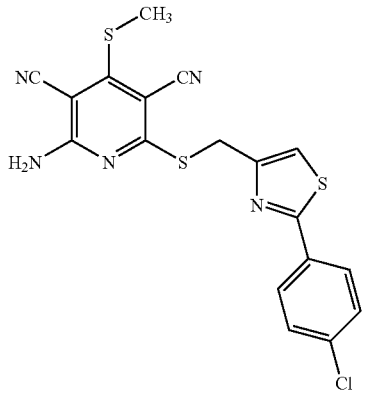

250 mg (1.13 mmol) of 2-amino-6-mercapto-4-(methylthio)pyridine-3,5-dicarbonitrile, 412 mg (1.69 mmol) of 4-(chloromethyl)-2-(4-chlorophenyl)-1,3-thiazole and 378 mg (4.50 mmol) of sodium bicarbonate are combined in 5 ml of DMF and stirred at room temperature for 12 h. A voluminous solid precipitates out, which solid is filtered off using a glass frit, washed three times with water and twice with diethyl ether and dried. This gives a white powder.

Yield: 474 mg (98% of theory)

$^1$H-NMR (400 MHz, CDCl$_3$): δ=8.13 (br. s, 2H), 7.93 (d, 2H), 7.87 (s, 1H), 7.55 (d, 2H), 4.59 (s, 2H), 2.72 (s, 3H).

LC-MS (Method 2): R$_t$=2.72 min; MS (ESIpos): m/z=430 [M+H]$^+$.

Example 3A

2-Amino-6-[({2-[4-fluorophenyl)amino]-1,3-thiazol-4-yl}methyl)thio]-4-(methylthio)pyridine-3,5-dicarbonitrile

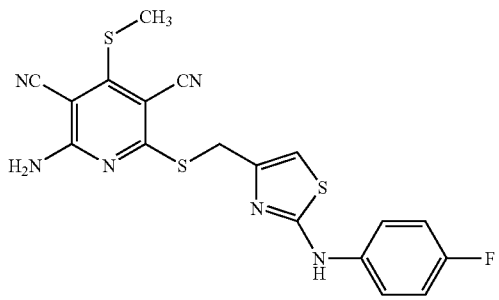

Example 3A is prepared analogously to Example 2A from 2-amino-6-mercapto-4-(methylthio)pyridine-3,5-dicarbonitrile and 4-(chloromethyl)-N-(4-fluorophenyl)-1,3-thiazole-2-amine hydrochloride, which is prepared in situ from 4-fluorophenylthiourea and 1,3-dichloroacetone (cf. WO 2006/027142, Example 5A).

Yield: 95% of theory $^1$H-NMR (400 MHz, CDCl$_3$): δ=10.21 (s, 1H), 8.10 (br. s, 2H), 7.55-7.63 (m, 2H), 7.08-7.14 (m, 2H), 6.91 (s, 1H), 4.42 (s, 2H), 3.73 (s, 3H).

LC-MS (Method 3): R$_t$=2.54 min; MS (ESIpos): m/z=429 [M+H]$^+$.

Example 4A

2-Chloro-6-({[2-(4-chlorophenyl)-1,3-thiazol-4-yl]methyl}thio)-4-(piperidin-1-yl)pyridine-3,5-dicarbonitrile

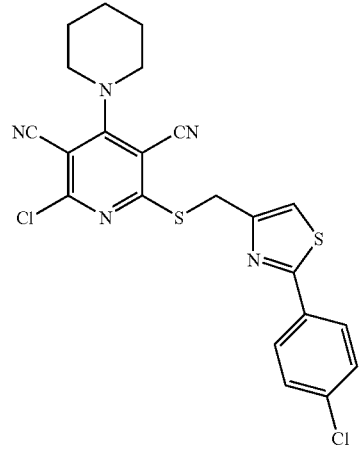

2.30 g (4.93 mmol) of the compound from Example 2 are added to a suspension of 3.85 g (29.55 mmol) of isopentyl nitrite and 3.97 g (29.55 mmol) of copper(II) chloride in 40 ml of dry acetonitrile, and the mixture is stirred at +60° C. for 3 h. 20 ml of 1 N hydrochloric acid are then added to the reaction solution. The aqueous phase is extracted twice with in each case 30 ml of ethyl acetate. The combined organic phases are washed once with 10 ml of saturated sodium bicarbonate solution and once with 10 ml of saturated sodium chloride solution and dried over magnesium sulfate. After removal of the solvent on a rotary evaporator, the crude product is purified chromatographically on silica gel 60 (mobile phase: gradient cyclohexane/ethyl acetate 10:1→1:4).

Yield: 1.50 g (59% of theory)

$^1$H-NMR (400 MHz, DMSO-d$_6$): δ=7.94 (d, 2H), 7.68 (s, 1H), 7.57 (d, 2H), 4.63 (s, 2H), 3.68-3.58 (br. s, 4H), 1.72-1.58 (br. s, 6H).

LC-MS (Method 2): R$_t$=3.23 min; MS (ESIpos): m/z=486 [M+H]$^+$.

The compounds listed in the table below are prepared analogously to Example 2A from the appropriate starting materials:

| Example No. | Structure (yield) | LC-MS: R$_t$ [min] (Method); MS (ESI): m/z [M + H]$^+$ | $^1$H-NMR (DMSO-d$_6$): δ = |
|---|---|---|---|
| 5A | (96% of theory) | 1.87 min (7); m/z = 335 | 8.28-7.93 (br. s, 1H), 6.97 (s, 2H), 6.59 (s, 1H), 4.27 (s, 2H), 2.73 (s, 3H). |

| Example No. | Structure (yield) | LC-MS: R_t [min] (Method); MS (ESI): m/z [M + H]+ | 1H-NMR (DMSO-d_6): δ = |
|---|---|---|---|
| 6A | 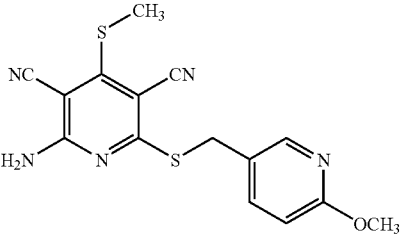 (90% of theory) | 3.43 min (5); m/z = 344 | 8.35 (d, 1H), 8.28-7.88 (br. s, 2H), 7.81 (dd, 1H), 6.77 (d, 1H), 4.49 (s, 2H), 3.81 (s, 3H), 2.72 (s, 3H). |
| 7A | 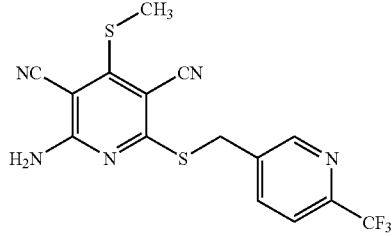 (90% of theory) | 3.63 min (5); m/z = 382 | 8.97 (d, 1H), 8.48-7.99 (br. s, 2H), 8.22 (dd, 1H), 7.84 (d, 1H), 4.54 (s, 2H), 2.72 (s, 3H). |
| 8A | 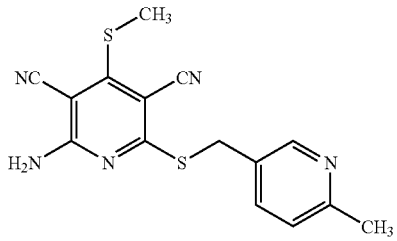 (84% of theory) | 1.96 min (5); m/z = 328 | 8.60 (d, 1H), 8.47-7.86 (br. s, 2H), 7.79 (dd, 1H), 7.18 (d, 1H), 4.41 (s, 2H), 2.72 (s, 3H), 2.42 (s, 3H). |
| 9A | 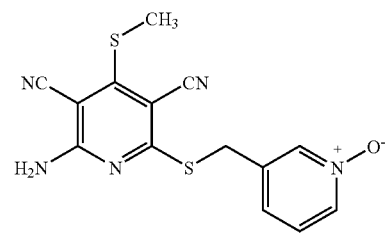 (90% of theory) | 2.15 min (7); m/z = 330 | |

Example 10A 2-({[2-(4-Chlorophenyl)-1,3-thiazol-4-yl]methyl}thio)-6-hydroxy-4-(piperidin-1-yl)pyridine-3,5-di-carbonitrile

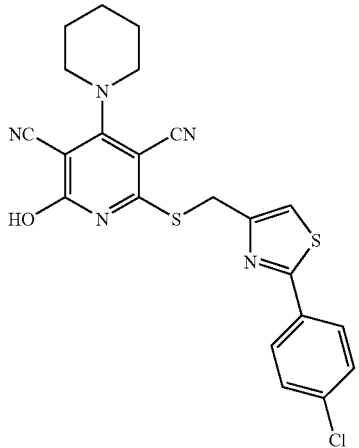

400 mg (0.82 mmol) of the compound from Example 4A are initially charged in 8 ml of dry DMF. After addition of 110 mg (0.99 mmol) of potassium tert-butoxide, the mixture is stirred at RT for RT. A solution of 74 mg (0.82 mmol) of methyl glycolate in 1 ml of dry DMF is then added dropwise, and the reaction mixture is stirred at RT for 20 h. The solvent is then removed on a rotary evaporator and the residue is directly purified by preparative HPLC (column: YMC GEL ODS-AQ S-5/15 μm; mobile phase gradient: acetonitrile/water 10:90→95:5).

Yield: 45 mg (20% of theory)

$^1$H-NMR (400 MHz, DMSO-$d_6$): δ=7.97 (d, 2H), 7.72 (s, 1H), 7.57 (d, 2H), 4.64 (s, 2H), 3.54-3.44 (br. s, 4H), 1.68-1.56 (br. s, 6H).

LC-MS (Method 5): $R_t$=4.18 min; MS (ESIpos): m/z=468 [M+H]$^+$.

Example 11A

2-Amino-6-({[2-(4-chlorophenyl)-1,3-oxazol-4-yl]methyl}sulfanyl)-4-(methylsulfanyl)pyridine-3,5-dicarbonitrile

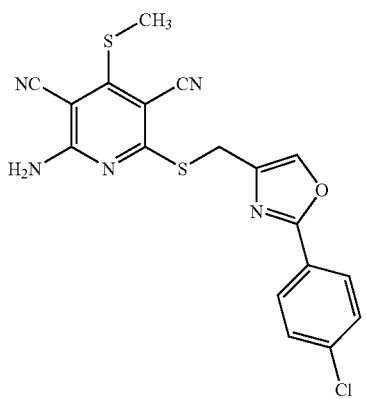

The title compound is prepared analogously to Example 2A from the appropriate starting materials.

Yield: 362 mg (88% of theory)

LC-MS (Method 8): $R_t$=2.27 min; MS (ESIpos): m/z=414 [M+H]$^+$.

Example 12A

2-Amino-6-{[(6-chloro-1-oxidopyridin-3-yl)methyl]sulfanyl}-4-(methylsulfanyl)pyridine-3,5-di-carbonitrile

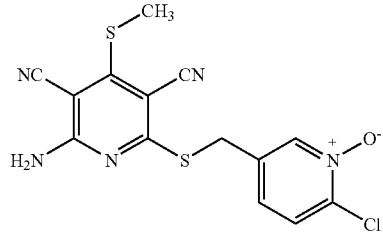

The title compound is prepared analogously to Example 2A from the appropriate starting materials. The starting material 2-chloro-5-(chloromethyl)pyridine 1-oxide can be obtained according to a literature procedure [J. W. Tilley, P. Levitan, R. W. Kierstaed, *J. Heterocycl. Chem.* 1979, 16, 333-337].

Yield: 267 mg (54% of theory)

$^1$H-NMR (400 MHz, CDCl$_3$): δ=8.73 (d, 1H), 8.12-7.85 (br. s, 2H), 7.72 (d, 1H), 7.49 (dd, 1H), 4.38 (s, 2H), 2.72 (s, 3H).

LC-MS (Method 5): $R_t$=2.67 min; MS (ESIpos): m/z=364 [M+H]$^+$.

WORKING EXAMPLES

Example 1

2-Amino-6-({[2-(4-chlorophenyl)-1,3-thiazol-4-yl]methyl}thio)-4-(4-hydroxypiperidin-1-yl)pyridine-3,5-dicarbonitrile

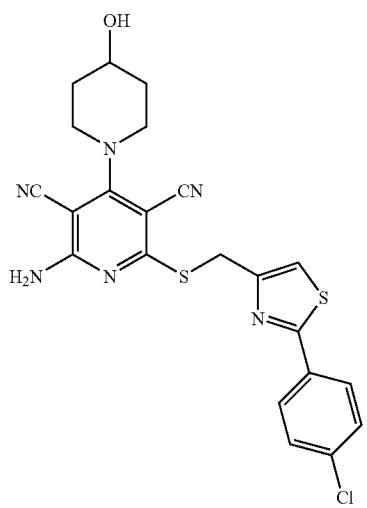

100 mg (0.23 mmol) of 2-amino-6-({[2-(4-chlorophenyl)-1,3-thiazol-4-yl]methyl}thio)-4-(methyl-thio)pyridine-3,5- dicarbonitrile and 1000 mg (9.89 mmol) of 4-hydroxypiperidine are combined in 2 ml of acetone and stirred under reflux for 8 h. The mixture is then added to a mixture of semiconcentrated aqueous ammonium chloride solution and ethyl acetate. After vigorous mixing, the organic phase is separated off, washed with saturated sodium chloride solution, dried over magnesium sulfate and filtered off using a glass frit, and the solvent is removed on a rotary evaporator. The residue is purified initially by column chromatography on silica gel 60 (mobile phase: gradient toluene/ethyl acetate 3:1→1:1) and then by preparative HPLC (column: YMC GEL ODS-AQ S-5/15 µm; mobile phase gradient: acetonitrile/water 10:90→95:5). The title compound in obtained as a white powder.

Yield: 40 mg (36% of theory)

$^1$H-NMR (400 MHz, DMSO-$d_6$): δ=7.93 (d, 2H), 7.82 (s, 1H), 7.67 (br. s, 2H), 7.56 (d, 2H), 4.54 (s, 2H), 3.68-3.75 (m, 3H), 3.25-3.35 (m, 2H), 1.80-1.88 (m, 2H), 1.44-1.57 (m, 2H).

LC-MS (Method 2): $R_t$=2.38 min; MS (ESIpos): m/z=483 [M+H]$^+$.

The compounds listed in the table below are prepared analogously to Example 1 from the appropriate starting materials:

| Example No. | Structure (yield) | LC-MS: $R_t$ [min] (Method); MS (ESI): m/z [M + H]$^+$ | $^1$H-NMR (DMSO-$d_6$): δ = |
|---|---|---|---|
| 2 | 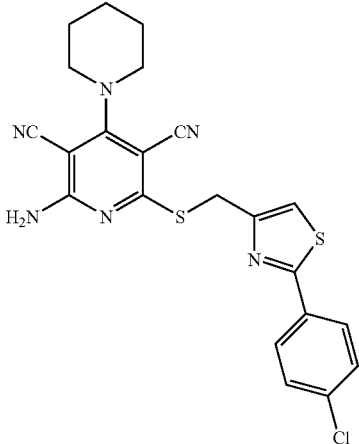<br>(53% of theory) | 2.95 min (2);<br>m/z = 467 | |
| 3 | 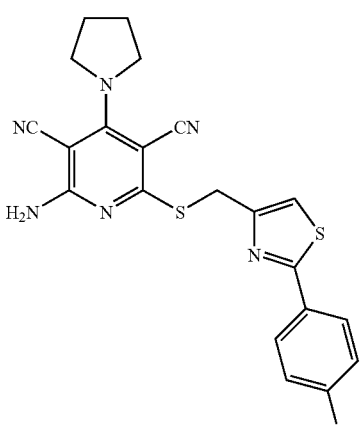<br>(41% of theory) | 3.06 min (4);<br>m/z = 453 | 7.92 (d, 2H), 7.79 (s, 1H), 7.58 (d, 2H), 7.39 (br. s, 2H), 4.51 (s, 2H), 3.80-3.88 (m, 4H), 1.84-1.88 (m, 4H). |

-continued
| Example No. | Structure (yield) | LC-MS: $R_t$ [min] (Method); MS (ESI): m/z [M + H]$^+$ | $^1$H-NMR (DMSO-d$_6$): δ = |
|---|---|---|---|
| 4 | 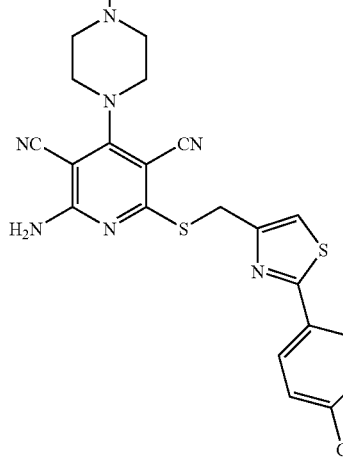 (40% of theory) | 1.64 min (3); m/z = 482 | 7.92 (d, 2H), 7.82 (s, 1H), 7.72 (br. s, 2H), 7.56 (d, 2H), 4.54 (s, 2H), 3.49-3.56 (m, 4H), 2.38-2.48 (m, 4H), 2.20 (s, 3H). |
| 5 | 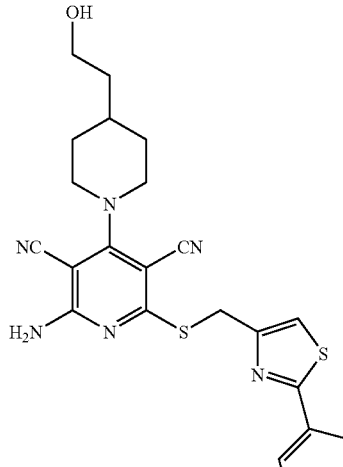 (37% of theory) | 2.54 min (2); m/z = 511 | |
| 6 | 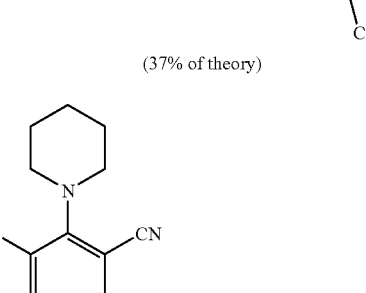 (97% of theory) | 2.89 min (4); m/z = 466 | |

-continued

| Example No. | Structure (yield) | LC-MS: R$_t$ [min] (Method); MS (ESI): m/z [M + H]$^+$ | $^1$H-NMR (DMSO-d$_6$): δ = |
|---|---|---|---|
| 7 | (18% of theory) | 1.67 min (2); m/z = 468 | 7.92 (d, 2H), 7.82 (s, 1H), 7.70 (br. s, 2H), 7.56 (d, 2H), 4.56 (s, 2H), 3.40-3.46 (m, 4H), 2.74-2.80 (m, 4H). |
| 8 | (43% of theory) | 1.63 min (2); m/z = 512 | |

| Example No. | Structure (yield) | LC-MS: R_t [min] (Method); MS (ESI): m/z [M + H]+ | $^1$H-NMR (DMSO-$d_6$): δ = |
|---|---|---|---|
| 9 | 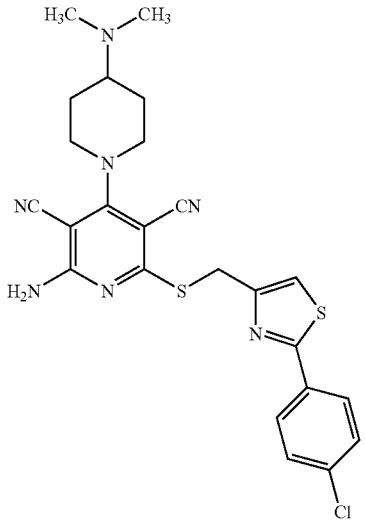 (41% of theory) | 1.70 min (3); m/z = 510 | |
| 10 | 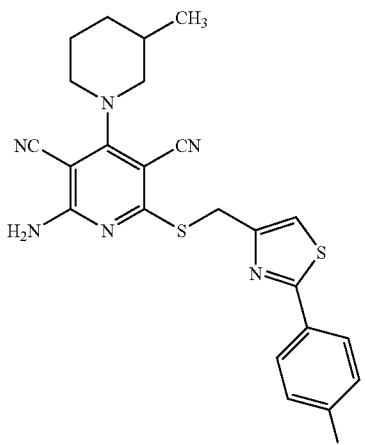 (52% of theory) | 3.26 min (4); m/z = 481 | |

| Example No. | Structure (yield) | LC-MS: R_t [min] (Method); MS (ESI): m/z [M + H]+ | $^1$H-NMR (DMSO-$d_6$): δ = |
|---|---|---|---|
| 11 | 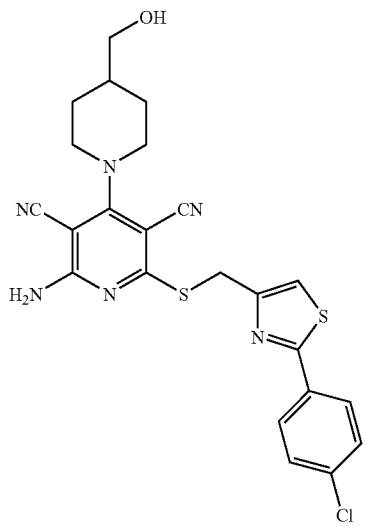<br>(15% of theory) | 2.45 min (2);<br>m/z = 497 | |
| 12 | 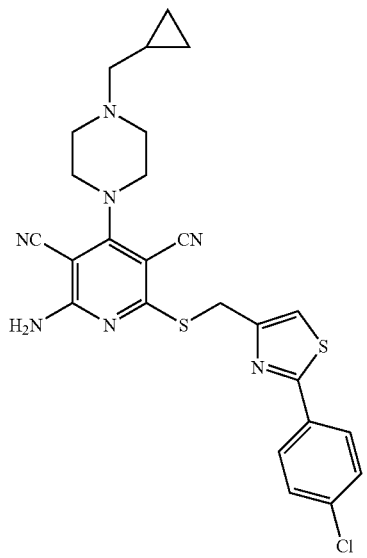<br>(17% of theory) | 1.78 min (3);<br>m/z = 522 | |

| Example No. | Structure (yield) | LC-MS: $R_t$ [min] (Method); MS (ESI): m/z [M + H]$^+$ | $^1$H-NMR (DMSO-d$_6$): δ = |
|---|---|---|---|
| 13 | 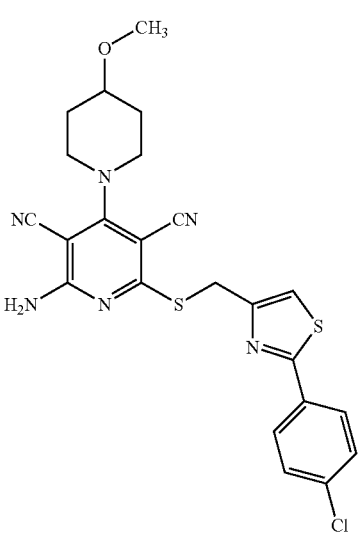<br>(26% of theory) | 2.87 min (3); m/z = 497 | 7.93 (d, 2H), 7.82 (s, 1H), 7.80-7.60 (br. s, 2H), 7.56 (d, 2H), 4.54 (s, 2H), 3.71-3.60 (m, 2H), 3.48-3.39 (m, 1H), 3.38-3.29 (m, 2H), 3.31 (s, 3H), 1.99-1.88 (m, 2H), 1.62-1.51 (m, 2H). |
| 14 | 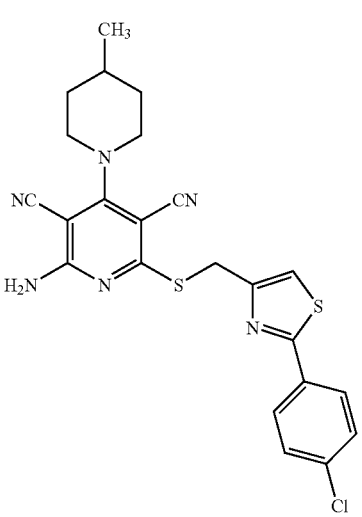<br>(40% of theory) | 3.07 min (2); m/z = 481 | |

| Example No. | Structure (yield) | LC-MS: $R_t$ [min] (Method); MS (ESI): m/z [M + H]$^+$ | $^1$H-NMR (DMSO-d$_6$): δ = |
|---|---|---|---|
| 15 | 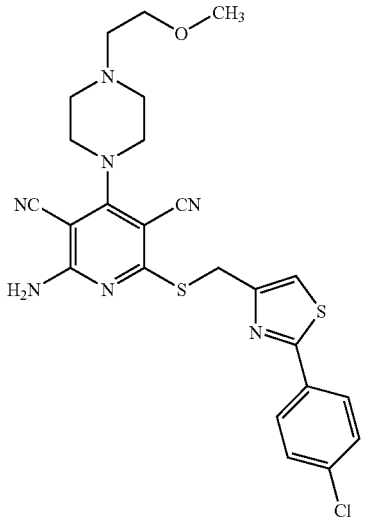<br>(35% of theory) | 1.72 min (2);<br>m/z = 526 | |
| 16 | 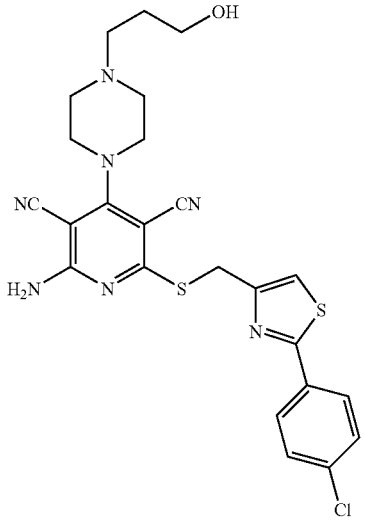<br>(30% of theory) | 1.80 min (4);<br>m/z = 526 | |

| Example No. | Structure (yield) | LC-MS: R_t [min] (Method); MS (ESI): m/z [M + H]+ | 1H-NMR (DMSO-d6): δ = |
|---|---|---|---|
| 17 | 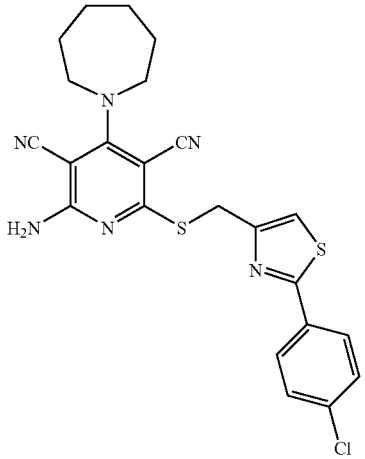 (12% of theory) | 3.20 min (4); m/z = 481 | |
| 18 | 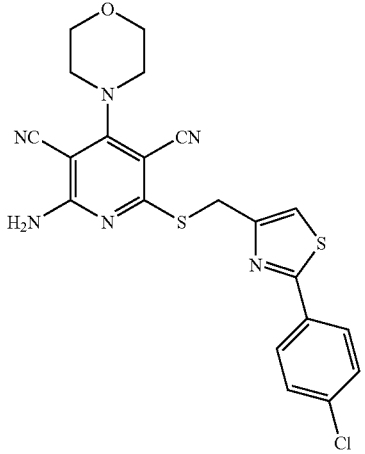 (31% of theory) | 3.96 min (5); m/z = 469 | 7.93 (d, 2H), 7.89-7.63 (br. s, 2H), 7.83 (s, 1H), 7.55 (d, 2H), 4.54 (s, 2H), 3.73-3.66 (m, 4H), 3.58-3.51 (m, 4H). |
| 19 | 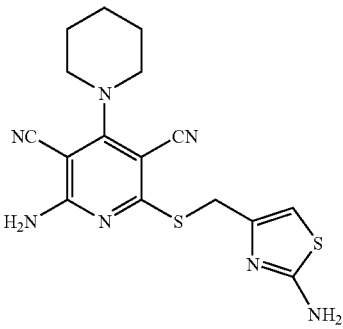 (69% of theory) | 2.27 min (7); m/z = 372 | 7.75-7.48 (br. s, 2H), 6.95 (s, 2H), 6.54 (s, 1H), 4.22 (s, 2H), 3.52-3.42 (br. s, 4H), 1.68-1.58 (br. s, 6H). |

-continued
| Example No. | Structure (yield) | LC-MS: $R_t$ [min] (Method); MS (ESI): m/z [M + H]$^+$ | $^1$H-NMR (DMSO-$d_6$): δ = |
|---|---|---|---|
| 20 | 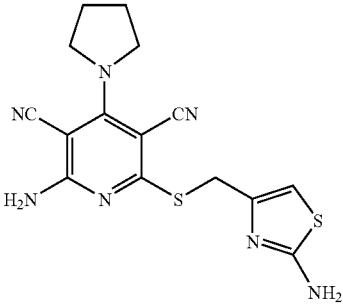<br>(28% of theory) | 1.58 min (4); m/z = 358 | 7.49-7.18 (br. s, 2H), 6.94 (s, 2H), 6.54 (s, 1H), 4.20 (s, 2H), 3.93-3.76 (br. s, 4H), 1.97-1.80 (br. s, 4H). |
| 21 | 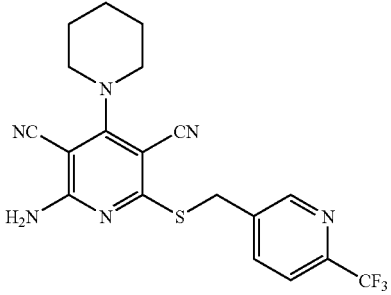<br>(42% of theory) | 3.91 min (5); m/z = 419 | 8.95 (s, 1H), 8.20 (dd, 1H), 7.88-7.59 (br. s, 2H), 7.83 (d, 1H), 4.48 (s, 2H), 3.52-3.42 (br. s, 4H), 1.65-1.57 (br. s, 6H). |
| 22 | 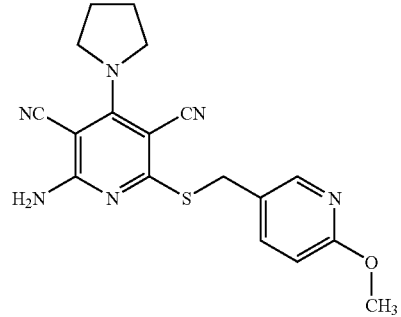<br>(13% of theory) | 2.40 min (4); m/z = 367 | 8.30 (d, 1H), 7.77 (dd, 1H), 7.53-7.39 (br. s, 2H), 6.76 (d, 1H), 4.31 (s, 2H), 3.87-3.79 (m, 4H), 1.91-1.83 (m, 4H). |
| 23 | 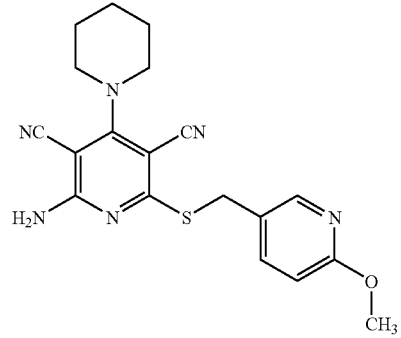<br>(37% of theory) | 3.70 min (5); m/z = 381 | 8.30 (d, 1H), 7.78 (dd, 1H), 7.75-7.58 (br. s, 2H), 6.75 (d, 1H), 4.34 (s, 2H), 3.81 (s, 3H), 3.50-3.43 (br. s, 4H), 1.67-1.58 (br. s, 6H). |

| Example No. | Structure (yield) | LC-MS: $R_t$ [min] (Method); MS (ESI): m/z [M + H]$^+$ | $^1$H-NMR (DMSO-d$_6$): δ = |
|---|---|---|---|
| 24 | (26% of theory) | 2.01 min (5); m/z = 351 | 8.57 (s, 1H), 7.73 (d, 1H), 7.58-7.29 (br. s, 2H), 7.16 (d, 1H), 4.35 (s, 2H), 3.88-3.77 (br. s, 4H), 1.93-1.82 (br. s, 4H). |
| 25 | (55% of theory) | 2.38 min (5); m/z = 365 | 8.55 (d, 1H), 7.79-7.52 (br. s, 2H), 7.74 (dd, 1H), 7.17 (d, 1H), 4.37 (s, 2H), 3.51-3.42 (br. s, 4H), 1.67-1.54 (br. s, 6H). |
| 26 | (11% of theory) | 2.05 min (2); m/z = 482 | |

| Example No. | Structure (yield) | LC-MS: $R_t$ [min] (Method); MS (ESI): m/z [M + H]$^+$ | $^1$H-NMR (DMSO-d$_6$): δ = |
|---|---|---|---|
| 27 | 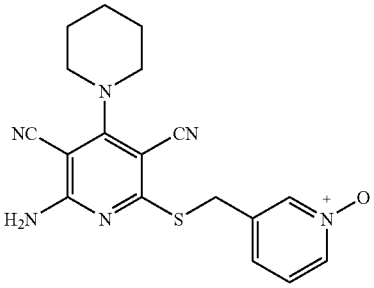<br>(30% of theory) | 2.00 min (4); m/z = 367 | 8.46 (s, 1H), 8.08 (d, 1H), 7.99-7.53 (br. s, 2H), 7.44 (d, 1H), 7.33 (pseudo-t, 1H), 4.35 (s, 2H), 3.53-3.43 (br. s, 4H), 1.68-1.57 (br. s, 6H). |
| 28 | 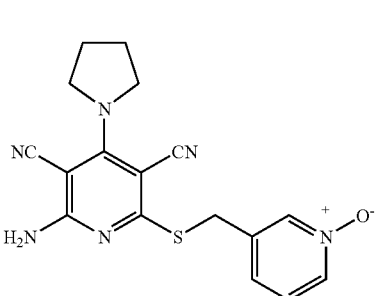<br>(57% of theory) | 1.81 min (4); m/z = 353 | 8.45 (s, 1H), 8.07 (d, 1H), 7.76-7.22 (br. s, 2H), 7.43 (d, 1H), 7.33 (pseudo-t, 1H), 4.32 (s, 2H), 3.87-3.80 (br. s, 4H), 1.92-1.83 (br. s, 4H). |

Example 29

N-[6-({[2-(4-Chlorophenyl)-1,3-thiazol-4-yl]methyl}thio)-3,5-dicyano-4-(piperidin-1-yl)pyridin-2-yl]-beta-alanine

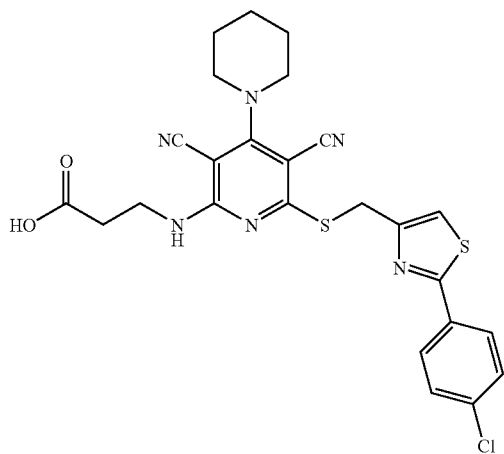

A solution of 70 mg (0.14 mmol) of the compound from Example 4A and 27 mg (0.30 mmol) of beta-alanine in 2 ml of DMF is stirred at RT for 8 h. The mixture is then stirred at +90° C. for 2 h. After cooling to RT the reaction mixture is purified directly by preparative HPLC (column: YMC GEL ODS-AQ S-5, 15 μm; mobile phase gradient: acetonitrile/water 10:90→95:5).

Yield: 42 mg (57% of theory)

$^1$H-NMR (400 MHz, DMSO-d$_6$): δ=12.26 (s, 1H), 7.93 (d, 2H), 7.71 (t, 1H), 7.62 (s, 1H), 7.56 (d, 2H), 4.62 (s, 2H), 3.72-3.63 (m, 2H), 3.53-3.43 (m, 4H), 3.36-3.25 (m, 2H), 1.68-1.57 (br. s, 6H).

LC-MS (Method 5): $R_t$=4.28 min; MS (ESIpos): m/z=539 [M+H]$^+$.

The compounds listed in the table below are prepared analogously to Example 29 from the appropriate starting materials:

| Example No. | Structure (yield) | LC-MS: R_t [min] (Method); MS (ESI): m/z [M + H]+ | $^1$H-NMR (DMSO-d$_6$): δ = |
|---|---|---|---|
| 30 | 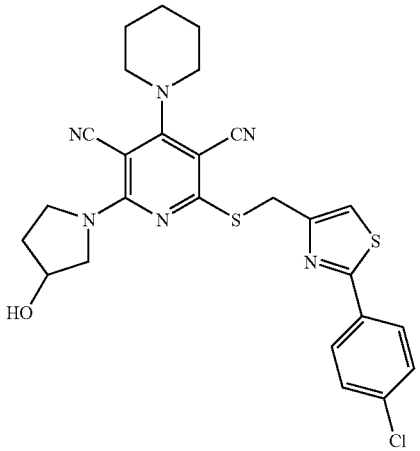<br>(78% of theory) | 2.89 min (2); m/z = 537 | 10.25 (s, 1H), 8.19 (br. s, 2H), 8.35 (d, 1H), 7.92 (dd, 1H), 7.68-7.58 (m, 2H), 7.19-7.08 (m, 2H), 7.11-7.07 (m, 2H), 4.89 (t, 1H), 4.45 (s, 2H), 4.38-4.30 (m, 2H), 3.78-3.68 (m, 2H). |
| 31 | 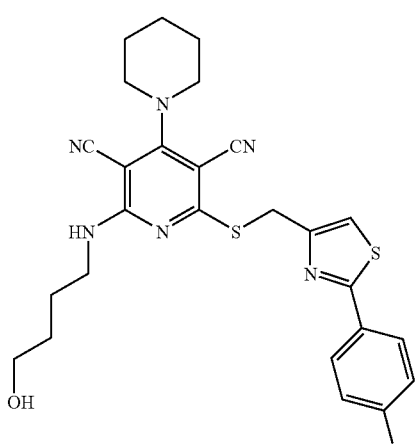<br>(88% of theory) | 4.40 min (5); m/z = 539 | 7.92 (d, 2H), 7.78 (t, 1H), 7.58 (s, 1H), 7.56 (d, 2H), 4.60 (s, 2H), 4.37 (t, 1H), 3.53-3.43 (br. s, 4H), 3.42-3.36 (m, 2H), 3.33-3.27 (m, 2H), 1.70-1.57 (br. s, 6H), 1.53-1.43 (m, 2H), 1.40-1.31 (m, 2H). |
| 32 | 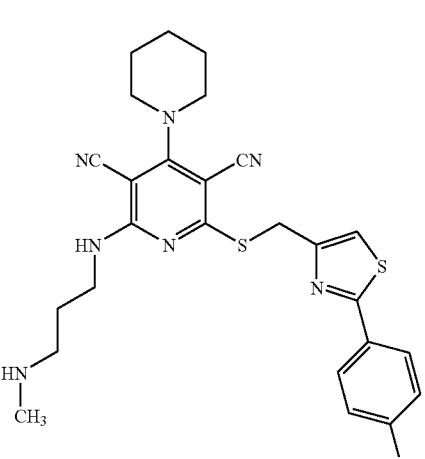<br>(27% of theory) | 2.00 min (4); m/z = 538 | |

| Example No. | Structure (yield) | LC-MS: $R_t$ [min] (Method); MS (ESI): m/z [M + H]$^+$ | $^1$H-NMR (DMSO-d$_6$): δ = |
|---|---|---|---|
| 33 | 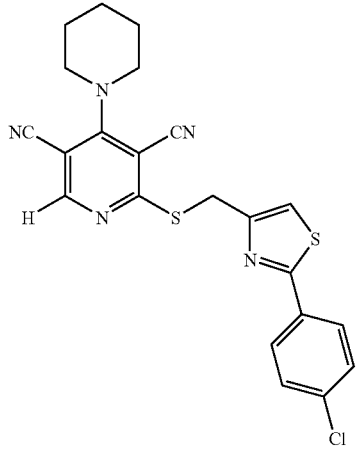 (9% of theory) | 3.29 min (4); m/z = 540 | |

Example 34

2-({[2-(4-Chlorophenyl)-1,3-thiazol-4-yl]methyl}thio)-4-(piperidin-1-yl)pyridine-3,5-dicarbonitrile

Example 35

2-({[2-(4-Chlorophenyl)-1,3-thiazol-4-yl]methyl}thio)-6-methoxy-4-(piperidin-1-yl)pyridine-3,5-dicarbonitrile

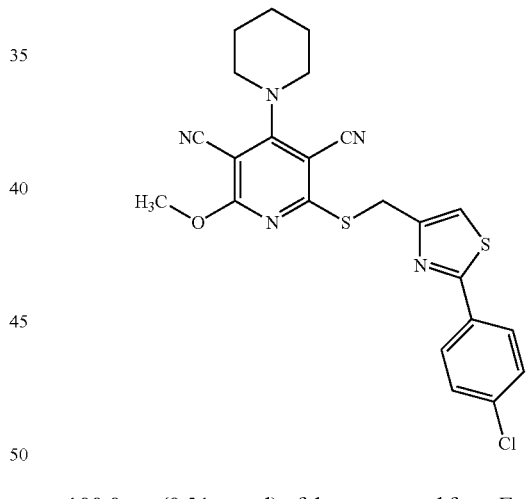

83.0 mg (0.16 mmol) of the compound from Example 2 are initially charged in 4 ml of dry THF. 130.7 mg (1.12 mmol) of isopentyl nitrite and 2.21 mg (0.02 mmol) of copper(II) chloride are added to this solution, and the mixture is stirred at RT for 20 h. The reaction mixture is then directly purified by preparative HPLC (column: YMC GEL ODS-AQ S-5, 15 μm; mobile phase gradient: acetonitrile/water 10:90→95:5).

Yield: 20.0 mg (27% of theory)

$^1$H-NMR (400 MHz, DMSO-d$_6$): δ=8.69 (s, 1H), 7.94 (d, 2H), 7.68 (s, 1H), 7.57 (d, 2H), 4.68 (s, 2H), 3.67-3.60 (br. s, 4H), 1.73-1.59 (br. s, 6H).

LC-MS (Method 2): $R_t$=3.14 min; MS (ESIpos): m/z=452 [M+H]$^+$.

100.0 mg (0.21 mmol) of the compound from Example 4A are initially charged in 2 ml of dry methanol. 12.2 mg (0.23 mmol) of sodium methoxide are added to this solution, and the mixture is stirred at +65° C. for 20 h. After cooling to RT the reaction mixture is stirred into 2 ml of water and stirred at RT for 1 h. The precipitate that is formed is filtered off with suction and washed with 1 ml of cold water. Purification is carried out by preparative HPLC (column: YMC GEL ODS-AQ S-5, 15 μm; mobile phase gradient: acetonitrile/water 10:90→95:5).

Yield: 14.0 mg (14% of theory)

$^1$H-NMR (400 MHz, DMSO-d$_6$): δ=7.96-7.91 (m, 2H), 7.68 (s, 1H), 7.60-7.54 (m, 2H), 4.70 (s, 2H), 3.62-3.53 (br. s, 4H), 1.68-1.48 (br. s, 6H).

LC-MS (Method 7): $R_t$=4.58 min; MS (ESIpos): m/z=482 [M+H]$^+$.

Example 36

Ethyl {[6-({[2-(4-chlorophenyl)-1,3-thiazol-4-yl]methyl}thio)-3,5-dicyano-4-(piperidin-1-yl)pyridin-2-yl]oxy}acetate

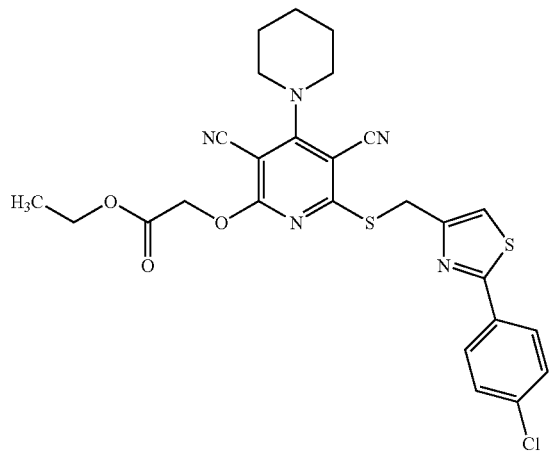

43 mg ethyl iodoacetate are initially charged in 2.4 ml of dry toluene. 47 mg (0.10 mmol) of the compound from Example 10A and 14 mg (0.05 mmol) of silver carbonate are then added. The reaction mixture is stirred with exclusion of light for 24 h. The mixture is then diluted with 1 ml of ethyl acetate, and 1 ml of saturated aqueous sodium bicarbonate solution is added. After separation of the phases the organic phase is dried over magnesium sulfate. The solvent is removed on a rotary evaporator and the residue is purified by preparative HPLC (column: YMC GEL ODS-AQ S-5/15 μm; mobile phase gradient: acetonitrile/water 10:90→95:5).

Yield: 35 mg (63% of theory)

$^1$H-NMR (400 MHz, DMSO-d$_6$): δ=7.93 (d, 2H), 7.74 (s, 1H), 7.57 (d, 2H), 5.12 (s, 2H), 4.58 (s, 2H), 4.11 (q, 2H), 3.66-3.57 (br. s, 4H), 1.71-1.61 (br. s, 6H), 1.12 (t, 3H).

LC-MS (Method 7): R$_t$=4.51 min; MS (ESIpos): m/z=554 [M+H]$^+$.

Example 37

2-Amino-6-({[2-(4-chlorophenyl)-1,3-oxazol-4-yl]methyl}sulfanyl)-4-(piperidin-1-yl)pyridine-3,5-dicarbonitrile

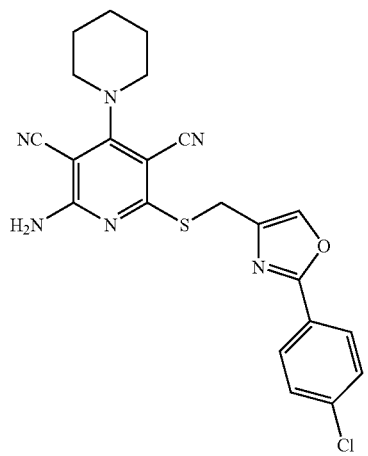

The title compound is prepared analogously to Example 1 from the appropriate starting materials.

Yield: 26 mg (12% of theory)

$^1$H-NMR (400 MHz, DMSO-d$_6$): δ=8.28 (s, 1H), 7.94 (d, 2H), 7.71-7.52 (br. s, 2H), 7.60 (d, 2H), 4.32 (s, 2H), 3.48 (br. s, 4H), 1.61 (br. s, 6H).

LC-MS (Method 9): R$_t$=1.47 min; MS (ESIpos): m/z=451 [M+H]$^+$.

Example 38

2-Amino-6-{[(1-oxido-6-piperidin-1-ylpyridin-3-yl)methyl]sulfanyl}-4-(piperidin-1-yl)pyridine-3,5-dicarbonitrile

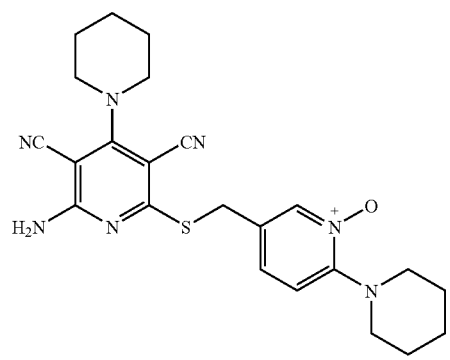

80 mg (0.22 mmol) of the compound from Example 12A are suspended in 1.9 ml of acetone, and 1.1 ml (10.99 mmol) of piperidine are added. The reaction mixture is stirred at RT for 12 h. After removal of the solvent on a rotary evaporator the residue is purified by preparative HPLC (column: YMC GEL ODS-AQ S-5/15 μm; mobile phase gradient: acetonitrile/water 10:90→95:5).

Yield: 27 mg (26% of theory)

$^1$H-NMR (400 MHz, DMSO-d$_6$): δ=8.33 (d, 1H), 7.96-7.61 (br. s, 2H), 7.35 (dd, 1H), 6.94 (d, 1H), 4.29 (s, 2H), 3.51-3.43 (br. s, 4H), 3.23-3.14 (br. s, 4H), 1.67-1.51 (br. s, 12H).

LC-MS (Method 5): R$_t$=3.41 min; MS (ESIpos): m/z=450 [M+H]$^+$.

Example 39

2-Amino-6-{[(1-oxido-6-pyrrolidin-1-ylpyridin-3-yl)methyl]sulfanyl}-4-(pyrrolidin-1-yl)pyridine-3,5-dicarbonitrile

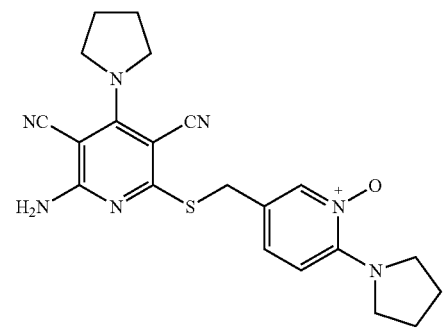

The title compound is prepared analogously to Example 38 from Example 12A and pyrrolidine.

Yield: 22 mg (23% of theory)

$^1$H-NMR (400 MHz, DMSO-d$_6$): δ=8.21 (s, 1H), 7.70-7.32 (br. s, 2H), 7.27 (dd, 1H), 6.77 (d, 1H), 4.24 (s, 2H), 3.89-3.78 (br. s, 4H), 3.54-3.43 (br. s, 4H), 1.93-1.83 (br. s, 4H), 1.83-1.76 (br. s, 4H).

LC-MS (Method 5): R$_t$=2.67 min; MS (ESIpos): m/z=422 [M+H]$^+$.

B. ASSESSING THE PHARMACOLOGICAL AND PHYSIOLOGICAL ACTIVITY

The pharmacological and physiological activity of the compounds according to the invention can be demonstrated in the following assays:

B-1. Indirect Determination of the Adenosine Agonism by Way of Gene Expression

Cells of the CHO (Chinese Hamster Ovary) permanent cell line are transfected stably with the cDNA for the adenosine receptor subtypes A1, A2a and A2b. The adenosine A1 receptors are coupled to the adenylate cyclase by way of G$_i$ proteins, while the adenosine A2a and A2b receptors are coupled by way of G$_s$ proteins. In correspondence with this, the formation of cAMP in the cell is inhibited or stimulated, respectively. After that, expression of the luciferase is modulated by way of a cAMP-dependent promoter. The luciferase test is optimized, with the aim of high sensitivity and reproducibility, low variance and good suitability for implementation on a robot system, by varying several test parameters, such as cell density, duration of the growth phase and the test incubation, forskolin concentration and medium composition. The following test protocol is used for pharmacologically characterizing cells and for the robot-assisted substance screening:

The stock cultures are grown, at 37° C. and under 5% CO$_2$, in DMEM/F12 medium containing 10% FCS (fetal calf serum) and in each case split 1:10 after 2-3 days. The test cultures are seeded in 384-well plates with 2000 cells per well and grown at 37° C. for approx. 48 hours. The medium is then replaced with a physiological sodium chloride solution (130 mM sodium chloride, 5 mM potassium chloride, 2 mM calcium chloride, 20 mM HEPES, 1 mM magnesium chloride hexahydrate, 5 mM sodium bicarbonate, pH 7.4). The substances to be tested, which are dissolved in DMSO, are pipetted into the test cultures (maximum final concentration of DMSO in the test mixture: 0.5%) in a dilution series of from $5\times10^{-11}$M to $3\times10^{-6}$M (final concentration). 10 minutes later, forskolin is added to the A1 cells and all the cultures are subsequently incubated at 37° C. for four hours. After that, 35 µl of a solution which is composed of 50% lysis reagent (30 mM disodium hydrogenphosphate, 10% glycerol, 3% TritonX100, 25 mM TrisHCl, 2 mM dithiothreitol (DTT), pH 7.8) and 50% luciferase substrate solution (2.5 mM ATP, 0.5 mM luciferin, 0.1 mM coenzyme A, 10 mM tricine, 1.35 mM magnesium sulfate, 15 mM DTT, pH 7.8) are added to the test cultures, which are shaken for approx 1 minute and the luciferase activity is measured using a camera system. The EC$_{50}$ values are determined, i.e., the concentrations at which 50% of the luciferase answer is inhibited in the case of the A1 cell, and, respectively, 50% of the maximum stimulation with the corresponding substance is achieved in the case of the A2b and A2a cells. The adenosine-analogous compound NECA (5-N-ethylcarboxamidoadenosine), which binds to all adenosine receptor subtypes with high affinity and possesses an agonistic effect, is used in these experiments as the reference compound [Klotz, K. N., Hessling, J., Hegler, J., Owman, C., Kull, B., Fredholm, B. B., Lohse, M. J., "Comparative pharmacology of human adenosine receptor subtypes—characterization of stably transfected receptors in CHO cells", *Naunyn Schmiedebergs Arch. Pharmacol.*, 357 (1998), 1-9).

Table 1 below lists the EC50 values of representative working examples for the receptor stimulation on adenosine A1, A2a and A2b receptor subtypes:

TABLE 1

| Example No. | EC$_{50}$ A1 [nM] (1 µM forskolin) | EC$_{50}$ A2a [nM] | EC$_{50}$ A2b [nM] |
|---|---|---|---|
| 1 | 1.3 | 686 | 116 |
| 2 | 0.5 | 385 | 44 |
| 4 | 12 | >3000 | >3000 |
| 6 | 45 | 1810 | >3000 |
| 27 | 0.3 | 63 | 0.9 |
| 30 | 5.7 | 1030 | 56 |
| 34 | 46 | >3000 | >3000 |
| 35 | 8.6 | >3000 | >3000 |
| 37 | 2.2 | 357 | 403 |

B-2. Studies on Isolated Blood Vessels

The caudal artery of anesthetized rats is excised and mounted in a conventional apparatus for measuring isolated blood vessels. The vessels are perfused in a heated bath and contracted using phenylephrine. The extent of the contraction is determined using a contraction meter. Test substances are added to the precontracted blood vessels, and the reduction of the contraction of the vessels is measured. A reduction of contraction corresponds to a dilation of the vessels. The concentration at which the contraction of the blood vessels is reduced by 50% is given as the EC$_{50}$ value of a test substance with respect to its relaxing properties.

B-3. Measurement of Blood Pressure and Heart Rate on Awake Rats

Various dosages of test substances are administered orally to awake SHR rats (spontaneously hypertensive rats) carrying an internal transmitter capable of measuring permanently both blood pressure and heart rate (telemetric monitoring of hemodynamic parameters. Blood pressure, heart rate and their changes are then recorded over a period of 24 hours.

B-4. Measurement of Blood Pressure and Heart Rate on Awake Marmosets

Various concentrations of the test substances are administered orally to awake marmosets which carry an internal transmitter capable of measuring permanently both blood pressure and heart rate (telemetric monitoring of hemodynamic parameters). Blood pressure, heart rate and their changes are then recorded for a period of 6-24 hours.

B-5. Determination of the Solubility

Reagents Required:

PBS buffer pH 7.4: weigh 90.00 g of NaCl p.a. (for example from Merck, Cat. No. 1.06404.1000), 13.61 g of KH$_2$PO$_4$ p.a. (for example from Merck, Cat. No. 1.04873.1000) and 83.35 g of 1 N NaOH (for example from Bernd Kraft GmbH, Cat. No. 01030.4000) into a 1 liter graduated flask, make up to the mark with water and stir for about 1 hour;

acetate buffer pH 4.6: weigh 5.4 g of sodium acetate× 3H$_2$O, analytical grade (e.g. from Merck, Cat. No. 1.06267.0500) into a 100 ml graduated flask, dissolve in 50 ml of water, add 2.4 g of glacial acetic acid, make up to 100 ml with water, check the pH and adjust to pH 4.6 if necessary;

dimethyl sulfoxide (for example from Baker, Art. No. 7157.2500);

distilled water.

Preparation of the Calibration Solutions:

Preparation of the starting solution for calibration solutions (stock solution): About 0.5 mg of the test substance is weighed accurately into a 2 ml Eppendorf safe-lock tube (from Eppendorf, Cat. No. 0030 120.094), DMSO is added to a concentration of 600 µg/ml (e.g. 0.5 mg of substance+833 µl of DMSO), and the mixture is agitated with a vortexer until dissolution is complete.

Calibration solution 1 (20 µg/ml): 34.4 µl of the stock solution are mixed with 1000 µl of DMSO and homogenized.

Calibration solution 2 (2.5 µg/ml): 100 µl of calibration solution 1 are mixed with 700 µl of DMSO and homogenized.

Preparation of the Sample Solutions:

Sample solution for solubility up to 10 g/l in PBS buffer pH 7.4: About 5 mg of the test substance are weighed accurately into a 2 ml Eppendorf safe-lock tube (from Eppendorf, Cat. No. 0030 120.094), and PBS buffer pH 7.4 is added to a concentration of 5 g/l (e.g. 5 mg of substance+500 µl of PBS buffer pH 7.4).

Sample solution for solubility up to 10 g/l in acetate buffer pH 4.6: About 5 mg of the test substance are weighed accurately into a 2 ml Eppendorf safe-lock tube (from Eppendorf, Cat. No. 0030 120.094), and acetate buffer pH 4.6 is added to a concentration of 5 g/l (e.g. 5 mg of substance+500 µl of acetate buffer pH 4.6).

Sample solution for solubility up to 10 g/l in water: About 5 mg of the test substance are weighed accurately into a 2 ml Eppendorf safe-lock tube (from Eppendorf, Cat. No. 0030 120.094), and water is added to a concentration of 5 g/l (e.g. 5 mg of substance+500 µl of water).

Procedure:

The sample solutions prepared in this way are shaken at 1400 rpm using a controlled-temperature shaker (e.g. Eppendorf thermomixer comfort Cat. No. 5355 000.011 with exchangeable block Cat. No. 5362.000.019) at 20° C. for 24 hours. 180 µl are removed from each of the solutions and transferred into Beckman polyallomer centrifuge tubes (Cat. No. 343621). These solutions are centrifuged at about 223 000×g for 1 hour (e.g. Beckman Optima L-90K ultracentrifuge with type 42.2 Ti rotor at 42 000 rpm). 100 µl of the supernatant are removed from each sample solution and diluted 1:5, 1:100 and 1:1000 with the solvent used in each case (water, PBS buffer 7.4 or acetate buffer pH 4.6). A portion of each dilution is dispensed into a suitable vessel for HPLC analysis.

Analysis:

The samples are analyzed by RP-HPLC. A two-point calibration plot of the test compound in DMSO is used for quantification. The solubility is expressed in mg/l. Analysis sequence: 1) calibration solution 2.5 mg/ml; 2) calibration solution 20 µg/ml; 3) sample solution 1:5; 4) sample solution 1:100; 5) sample solution 1:1000.

HPLC Method for Acids:

Agilent 1100 with DAD (G1315A), quat. pump (G1311A), autosampler CTC HTS PAL, degasser (G1322A) and column thermostat (G1316A); column: Phenomenex Gemini C18, 50 mm×2 mm, 5µ; temperature: 40° C.; eluent A: water/phosphoric acid pH 2; eluent B: acetonitrile; flow rate: 0.7 ml/min; gradient: 0-0.5 min 85% A, 15% B; ramp: 0.5-3 min 10% A, 90% B; 3-3.5 min 10% A, 90% B; ramp: 3.5-4 min 85% A, 15% B; 4-5 min 85% A, 15% B.

HPLC Method for Bases:

Agilent 1100 with DAD (G1315A), quat. pump (G1311A), autosampler CTC HTS PAL, degasser (G1322A) and column thermostat (G1316A); column: VDSoptilab Kromasil 100 C18, 60 mm×2.1 mm, 3.5µ; temperature: 30° C.; eluent A: water+5 ml perchloric acid/l; eluent B: acetonitrile; flow rate: 0.75 ml/min; gradient: 0-0.5 min 98% A, 2% B; ramp: 0.5-4.5 min 10% A, 90% B; 4.5-6 min 10% A, 90% B; ramp: 6.5-6.7 min 98% A, 2% B; 6.7-7.5 min 98% A, 2% B.

B-6. Determination of Pharmacokinetic Parameters after Intravenous and Oral Administration The substance to be tested is administered intravenously as a solution to animals (for example mice, rats, dogs), and oral administration takes place as solution or suspension by gavage. After administration of the substance, blood is taken from the animals at fixed times and is heparinized, and then plasma is obtained therefrom by centrifugation. The substance is quantified analytically in the plasma by LC/MS-MS. The plasma concentration/time courses found in this way are used to calculate the pharmacokinetic parameters such as AUC, $C_{max}$, $T_{1/2}$ (half-life) and CL (clearance) by means of a validated pharmacokinetic computer program.

C. WORKING EXAMPLES OF PHARMACEUTICAL COMPOSITIONS

The compounds of the invention can be converted into pharmaceutical preparations in the following ways:

Tablet:
Composition:

100 mg of the compound of the invention, 50 mg of lactose (monohydrate), 50 mg of maize starch (native), 10 mg of polyvinylpyrrolidone (PVP 25) (from BASF, Ludwigshafen, Germany) and 2 mg of magnesium stearate.

Tablet weight 212 mg, diameter 8 mm, radius of curvature 12 mm

Production:

The mixture of compound of the invention, lactose and starch is granulated with a 5% strength solution (m/m) of the PVP in water. The granules are dried and mixed with the magnesium stearate for 5 minutes. This mixture is compressed in a conventional tablet press (see above for format of the tablet). A guideline compressive force for the compression is 15 kN.

Suspension which can be Administered Orally:
Composition:

1000 mg of the compound of the invention, 1000 mg of ethanol (96%), 400 mg of Rhodigel® (xanthan gum from FMC, Pennsylvania, USA) and 99 g of water.

10 ml of oral suspension correspond to a single dose of 100 mg of the compound of the invention.

Production:

The Rhodigel is suspended in ethanol, and the compound of the invention is added to the suspension. The water is added while stirring. The mixture is stirred for about 6 h until the swelling of the Rhodigel is complete.

Solution which can be Administered Orally:
Composition:

500 mg of the compound of the invention, 2.5 g of polysorbate and 97 g of polyethylene glycol 400.20 g of oral solution correspond to a single dose of 100 mg of the compound of the invention.

Production:

The compound of the invention is suspended in the mixture of polyethylene glycol and polysorbate with stirring. The stirring process is continued until the compound of the invention has completely dissolved.

i.v. Solution:

The compound of the invention is dissolved in a concentration below the saturation solubility in a physiologically tolerated solvent (e.g. isotonic saline, 5% glucose solution and/or 30% PEG 400 solution). The solution is sterilized by filtration and used to fill sterile and pyrogen-free injection containers.

The invention claimed is:
1. A compound of the formula (I)

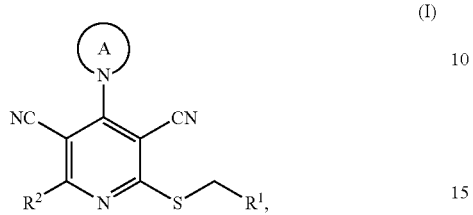

in which
ring A represents a 4- to 7-membered saturated heterocycle which is attached via nitrogen and which may contain a further ring heteroatom from the group consisting of N, O and S and which may be
(i) substituted up to five times by identical or different substituents from the group consisting of $(C_1-C_4)$-alkyl which for its part may be mono- or disubstituted by identical or different substituents from the group consisting of oxo, hydroxyl, $(C_1-C_4)$-alkoxy, amino, mono-$(C_1-C_4)$-alkylamino, di-$(C_1-C_4)$-alkylamino and $(C_3-C_6)$-cycloalkyl,
and/or
(ii) mono- or disubstituted by identical or different substituents from the group consisting of oxo, thioxo, hydroxyl, $(C_1-C_4)$-alkoxy, amino, mono-$(C_1-C_4)$-alkylamino, di-$(C_1-C_4)$-alkylamino and $(C_3-C_6)$-cyclo-alkyl,
$R^1$ represents 5- to 10-membered heteroaryl having one or two ring heteroatoms selected from the group consisting of N, O, and S, each of which radicals may be
(i) mono- or disubstituted by identical or different radicals selected from the group consisting of halogen, nitro, cyano, $(C_1-C_6)$-alkyl, trifluoromethyl, hydroxyl, $(C_1-C_6)$-alkoxy, amino, mono-$(C_1-C_6)$-alkylamino, di-$(C_1-C_6)$-alkylamino, mono-$(C_1-C_6)$-alkenylamino, carboxyl, $(C_1-C_6)$-alkoxycarbonyl, carbamoyl, mono-$(C_1-C_6)$-alkylaminocarbonyl and di-$(C_1-C_6)$-alkylaminocarbonyl
and/or
(ii) substituted by pyrrolidino, piperidino, morpholino, piperazino, N'-$(C_1-C_4)$-alkylpiperazino or a group of the formula -L-$R^3$ in which
L represents a bond, NH or O
and
$R^3$ represents phenyl or 5- or 6-membered heteroaryl having up to three ring heteroatoms from the group consisting of N, O and S, each of which radicals may be mono- to trisubstituted by identical or different radicals selected from the group consisting of halogen, nitro, cyano, $(C_1-C_6)$-alkyl, trifluoromethyl, hydroxyl, $(C_1-C_6)$-alkoxy, difluoromethoxy, trifluoromethoxy, amino, mono-$(C_1-C_6)$-alkylamino, di-$(C_1-C_6)$-alkylamino, $(C_1-C_6)$-alkoxycarbonyl and carboxyl,
and
$R^2$ represents hydrogen or represents $(C_1-C_6)$-alkyl or $(C_1-C_6)$-alkoxy, each of which radicals may be substituted by hydroxyl, $(C_1-C_4)$-alkoxy, carboxyl, $(C_1-C_4)$-alkoxycarbonyl or up to three times by fluorine
or
$R^2$ represents a group of the formula —$NR^4R^5$ in which
$R^4$ and $R^5$ are identical or different and independently of one another represent hydrogen or $(C_1-C_6)$-alkyl which may be mono- or disubstituted by identical or different radicals from the group consisting of hydroxyl, $(C_1-C_4)$-alkoxy, amino, mono-$(C_1-C_4)$-alkylamino, di-$(C_1-C_4)$-alkylamino, carboxyl, $(C_1-C_4)$-alkoxycarbonyl and a 4- to 7-membered heterocycle,
where the heterocycle mentioned contains one or two ring heteroatoms from the group consisting of N, O and S and for its part may be mono- or disubstituted by identical or different radicals from the group consisting of $(C_1-C_4)$-alkyl, hydroxyl, oxo and $(C_1-C_4)$-alkoxy,
or
$R^4$ and $R^5$ together with the nitrogen atom, to which they are attached, form a 4- to 7-membered heterocycle which may contain a further ring heteroatom from the group consisting of N, O or S and may be mono- or disubstituted by identical or different radicals from the group consisting of $(C_1-C_4)$-alkyl, hydroxyl, oxo, $(C_1-C_4)$-alkoxy, azetidino, pyrrolidino, piperidino and morpholino,
and salts, N-oxides, and salts of the N-oxides thereof.
2. The compound of the formula (I) as claimed in claim 1 in which
$R^1$ represents 5- or 6-membered heteroaryl having one or two ring heteroatoms selected from the group consisting of N, O, and S, each of which radicals is
(i) mono- or disubstituted by identical or different radicals selected from the group consisting of halogen, nitro, cyano, $(C_1-C_6)$-alkyl, trifluoromethyl, hydroxyl, $(C_1-C_6)$-alkoxy, amino, mono-$(C_1-C_6)$-alkylamino, di-$(C_1-C_6)$-alkylamino, mono-$(C_2-C_6)$-alkenylamino, carboxyl, $(C_1-C_6)$-alkoxycarbonyl, carbamoyl, mono-$(C_1-C_6)$-alkylaminocarbonyl and di-$(C_1-C_6)$-alkylaminocarbonyl
and/or
(ii) substituted by pyrrolidino, piperidino, morpholino, piperazino, N'-$(C_1-C_4)$-alkylpiperazino or a group of the formula -L-$R^3$ in which
L represents a bond, NH or O
and
$R^3$ represents phenyl or 5- or 6-membered heteroaryl having up to three ring heteroatoms from the group consisting of N, O and S, each of which radicals may be mono- to trisubstituted by identical or different radicals selected from the group consisting of halogen, nitro, cyano, $(C_1-C_6)$-alkyl, trifluoromethyl, hydroxyl, $(C_1-C_6)$-alkoxy, difluoromethoxy, trifluoromethoxy, amino, mono-$(C_1-C_6)$-alkylamino, di-$(C_1-C_6)$-alkylamino, $(C_1-C_6)$-alkoxycarbonyl and carboxyl,
or
$R^1$ represents N-oxidopyridyl.
3. The compound of the formula (I) of claim 1 in which
ring A represents a 5- to 7-heteroatom saturated heterocycle which is attached via nitrogen and which may contain a further ring heteroatom from the group consisting of N and O and which may be
(i) substituted up to five times by identical or different substituents from the group consisting of $(C_1-C_3)$-alkyl which for its part may be mono- or disubstituted by identical or different substituents from the group consisting of oxo, hydroxyl, $(C_1-C_3)$-alkoxy, amino, mono-$(C_1-C_3)$-alkylamino, di-$(C_1-C_3)$-alkylamino and $(C_3-C_5)$-cycloalkyl, and/or
(ii) mono- or disubstituted by identical or different radicals selected from the group consisting of oxo, hydroxyl, $(C_1-C_3)$-alkoxy, amino, mono-$(C_1-C_3)$-alkylamino, di-$(C_1-C_3)$-alkylamino and $(C_3-C_5)$-cycloalkyl, $R^1$ represents 5- or 6-membered heteroaryl having one or two ring heteroatoms selected from the group consisting of N, O, and S, each of which radicals is
(i) mono- or disubstituted by identical or different radicals selected from the group consisting of fluorine, chlorine, cyano, $(C_1-C_4)$-alkyl, amino, mono-$(C_1-C_4)$-alkylamino and di-$(C_1-C_4)$-alkylamino
and/or
(ii) substituted by morpholino, N'-$(C_1-C_4)$-alkylpiperazino or a group of the formula -L-$R^3$ in which
L represents a bond or NH
and
$R^3$ represents phenyl or 5- or 6-membered heteroaryl having up to three ring heteroatoms from the group consisting of N, O and S, each of which radicals may be mono- to trisubstituted by identical or different radicals selected from the group consisting of fluorine, chlorine, cyano, $(C_1-C_4)$-alkyl, trifluoromethyl, $(C_1-C_4)$-alkoxy, trifluoromethoxy and carboxyl,
or
$R^1$ represents N-oxidopyridyl,
and
$R^2$ represents hydrogen or represents $(C_1-C_4)$-alkoxy which may be substituted up to three times by fluorine
or
$R^2$ represents a group of the formula —$NR^4R^5$ in which
$R^4$ represents hydrogen or $(C_1-C_4)$-alkyl which may be substituted by hydroxyl, $(C_1-C_4)$-alkoxy, amino, mono-$(C_1-C_4)$-alkylamino, di-$(C_1-C_4)$-alkylamino, carboxyl, $(C_1-C_4)$-alkoxycarbonyl or a 5- or 6-membered heterocycle,
where the heterocycle mentioned contains one or two ring heteroatoms from the group consisting of N and O and for its part may be mono- or disubstituted by identical or different radicals from the group consisting of methyl, ethyl, hydroxyl, methoxy and ethoxy,
$R^5$ represents hydrogen or methyl
or
$R^4$ and $R^5$ together with the nitrogen atom, to which they are attached, form a 5- or 6-membered heterocycle which may contain a further ring heteroatom from the group consisting of N or O and may be mono- or disubstituted by identical or different radicals from the group consisting of methyl, ethyl, hydroxyl, methoxy and ethoxy.

4. The compound of the formula (I) of claim 1 in which ring A represents a group of the formula

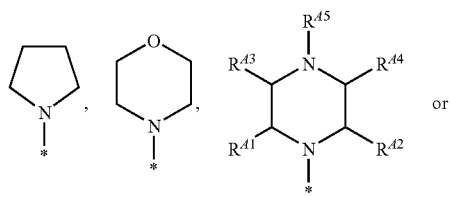

or

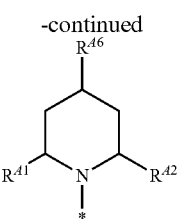

in which
* denotes the point of attachment to the pyridine ring,
$R^{41}$, $R^{42}$, $R^{43}$ and $R^{44}$ independently of one another represent hydrogen or methyl,
$R^{45}$ represents hydrogen, methyl, ethyl, 2-hydroxyethyl or cyclopropylmethyl
and
$R^{46}$ represents hydrogen, methyl, ethyl, hydroxymethyl, 2-hydroxyethyl, cyclopropylmethyl, hydroxyl, methoxy or ethoxy,
$R^1$ represents oxazolyl, thiazolyl or pyridyl, each of which radicals is
(i) mono- or disubstituted by identical or different radicals selected from the group consisting of fluorine, chlorine, methyl and amino
or
(ii) substituted by a group of the formula -L-$R^3$ in which
L represents a bond or NH
and
$R^3$ represents phenyl or pyridyl, each of which radicals may be mono- or disubstituted by identical or different radicals selected from the group consisting of fluorine, chlorine, cyano, methyl and methoxy,
or
$R^1$ represents N-oxidopyridyl,
and
$R^2$ represents hydrogen, methoxy or a group of the formula —$NR^4R^5$ in which
$R^4$ represents hydrogen or $(C_1-C_4)$-alkyl which may be substituted by hydroxyl, amino, methylamino, ethylamino, dimethylamino or diethylamino,
$R^5$ represents hydrogen
or
$R^4$ and $R^5$ together with the nitrogen atom to which they are attached form a group of the formula

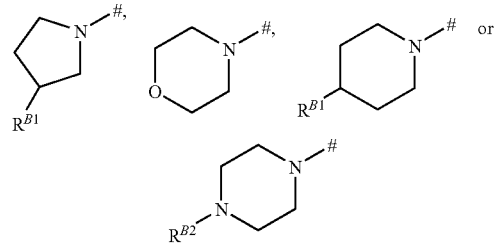

in which
# denotes the point of attachment to the pyridine ring,
$R^{B1}$ represents hydrogen or hydroxyl
and
$R^{B2}$ represents hydrogen or methyl.

5. A process for preparing the compounds of the formula (I) of claim 1 in which $R^2$ represents $NH_2$, wherein the compound of the formula (II)

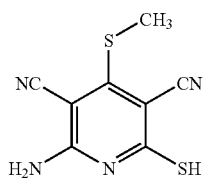
(II)

is initially, in an inert solvent in the presence of a base, reacted with a compound of the formula (III)

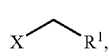
(III)

in which R¹ has the meaning given in claim 1 and
X represents a suitable leaving group such as halogen, mesylate, tosylate or triflate,
to give a compound of the formula (IV)

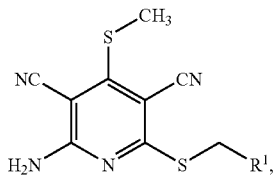
(IV)

in which R¹ has the meaning given above, and this compound is then, in an inert solvent or without further solvent, reacted with a compound of the formula (V)

(V)

in which ring A has the meaning given in claim 1,
to give a compound of the formula (I-A)

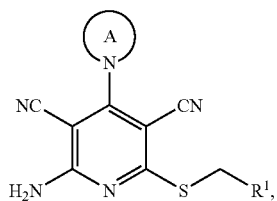
(I-A)

in which R¹ and ring A have the meanings given above,
and the compounds of the formula (I-A) are, if appropriate, converted with the appropriate (i) solvents and/or (ii) bases or acids into their salts, N-oxides, or salts of N-oxides.

6. A pharmaceutical composition comprising a compound according to claim 1 and an inert nontoxic pharmaceutically suitable auxiliary.

\* \* \* \* \*